United States Patent
Hestad et al.

(10) Patent No.: US 7,892,174 B2
(45) Date of Patent: Feb. 22, 2011

(54) SURGICAL ACCESS SYSTEM AND METHOD OF USING THE SAME

(75) Inventors: Hugh D. Hestad, Edina, MN (US); Rajesh Dwarakanath, Bloomington, MN (US); Daniel Robbins, North Bennington, VT (US); Deborah Lynn Hoch, Minneapolis, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1072 days.

(21) Appl. No.: 11/623,937

(22) Filed: Jan. 17, 2007

(65) Prior Publication Data

US 2008/0021284 A1 Jan. 24, 2008

Related U.S. Application Data

(63) Continuation-in-part of application No. 11/619,214, filed on Jan. 3, 2007, which is a continuation-in-part of application No. 11/458,662, filed on Jul. 19, 2006, now abandoned.

(51) Int. Cl.
 *A61B 1/32* (2006.01)
(52) U.S. Cl. .............. 600/214; 600/210; 600/213; 600/215; 600/219
(58) Field of Classification Search ......... 600/185–249; 606/57, 282, 90, 105
See application file for complete search history.

(56) References Cited

U.S. PATENT DOCUMENTS

| | | | | |
|---|---|---|---|---|
| 402,068 | A * | 4/1889 | Crannell | 600/243 |
| 421,814 | A * | 2/1890 | Bunce | 600/243 |
| 1,963,173 | A * | 6/1934 | Morin | 600/233 |
| 2,473,266 | A * | 6/1949 | Wexler | 600/215 |
| 3,509,873 | A * | 5/1970 | Karlin et al. | 600/226 |
| 3,572,326 | A * | 3/1971 | Jensen | 600/233 |
| 3,724,449 | A * | 4/1973 | Gauthier | 600/215 |
| 4,813,401 | A * | 3/1989 | Grieshaber | 600/234 |
| 5,293,863 | A | 3/1994 | Zhu et al. | |
| 5,299,563 | A * | 4/1994 | Seton | 600/215 |

(Continued)

FOREIGN PATENT DOCUMENTS

EP 1 192 905 4/2002

OTHER PUBLICATIONS

Blaine Copenheaver; International Search Report and Written Opinion; Dec. 6, 2007; 9 pages; PCT.

*Primary Examiner*—Eduardo C Robert
*Assistant Examiner*—Ellen C Hammond
(74) *Attorney, Agent, or Firm*—Seager, Tufte & Wickhem, LLC

(57) ABSTRACT

A surgical access system includes retractor for creating an access path between an incision site and a surgical site. The retractor includes a frame having a base member and a pair of generally curved rails extending therefrom. A tubular member is coupled to the frame and includes first and second blade portions that are capable of relative movement with respect to each other by movement on the curved rails. A method of inserting the retractor into a patient includes inserting a guide rod over a guide wire, locating an obturator in the retractor, inserting the obturator and retractor over the guide rod, and removing both the guide rod and obturator to leave the retractor in the body to provide the access path.

4 Claims, 16 Drawing Sheets

U.S. PATENT DOCUMENTS

| | | | |
|---|---|---|---|
| 5,503,617 A * | 4/1996 | Jako | 600/201 |
| 5,520,610 A * | 5/1996 | Giglio et al. | 600/233 |
| 5,667,481 A | 9/1997 | Villalta et al. | |
| 5,697,891 A * | 12/1997 | Hori | 600/245 |
| 5,728,046 A | 3/1998 | Mayer et al. | |
| 5,779,629 A * | 7/1998 | Hohlen | 600/233 |
| 5,792,044 A | 8/1998 | Foley et al. | |
| 5,813,978 A | 9/1998 | Jako | |
| 5,902,233 A * | 5/1999 | Farley et al. | 600/213 |
| 5,928,139 A | 7/1999 | Koros et al. | |
| 5,938,592 A | 8/1999 | Koteles et al. | |
| 5,967,972 A | 10/1999 | Santilli et al. | |
| 6,083,154 A * | 7/2000 | Liu et al. | 600/234 |
| 6,099,547 A | 8/2000 | Gellman et al. | |
| 6,187,000 B1 | 2/2001 | Davison et al. | |
| 6,190,312 B1 * | 2/2001 | Fowler, Jr. | 600/231 |
| 6,224,545 B1 | 5/2001 | Cocchia et al. | |
| 6,264,605 B1 * | 7/2001 | Scirica et al. | 600/227 |
| 6,280,379 B1 * | 8/2001 | Resnick | 600/220 |
| 6,361,492 B1 * | 3/2002 | Santilli | 600/205 |
| 6,371,968 B1 | 4/2002 | Kogasaka et al. | |
| 6,520,907 B1 | 2/2003 | Foley et al. | |
| 6,793,656 B1 | 9/2004 | Mathews | |
| 6,811,558 B2 | 11/2004 | Davison et al. | |
| 6,869,398 B2 | 3/2005 | Obenchain et al. | |
| 6,945,933 B2 | 9/2005 | Branch et al. | |
| 7,041,055 B2 | 5/2006 | Young et al. | |
| 2001/0007052 A1 * | 7/2001 | Person | 600/231 |
| 2002/0128659 A1 | 9/2002 | Michelson | |
| 2002/0177753 A1 * | 11/2002 | Dobrovolny | 600/234 |
| 2003/0149341 A1 * | 8/2003 | Clifton | 600/210 |
| 2003/0191371 A1 | 10/2003 | Smith et al. | |
| 2003/0199874 A1 | 10/2003 | Michelson | |
| 2004/0024291 A1 | 2/2004 | Zinkel | |
| 2004/0087833 A1 | 5/2004 | Bauer et al. | |
| 2004/0093001 A1 | 5/2004 | Hamada | |
| 2004/0147812 A1 | 7/2004 | Hamel | |
| 2004/0176665 A1 | 9/2004 | Branch et al. | |
| 2004/0215199 A1 | 10/2004 | Zinkel | |
| 2004/0236317 A1 | 11/2004 | Davison | |
| 2005/0038440 A1 | 2/2005 | Larson et al. | |
| 2005/0043741 A1 | 2/2005 | Michelson | |
| 2005/0043742 A1 | 2/2005 | Bruneau et al. | |
| 2005/0080320 A1 | 4/2005 | Lee et al. | |
| 2005/0113644 A1 | 5/2005 | Obenchain et al. | |
| 2005/0137461 A1 | 6/2005 | Marchek et al. | |
| 2005/0149035 A1 | 7/2005 | Pimenta et al. | |
| 2005/0159650 A1 | 7/2005 | Raymond et al. | |
| 2005/0159651 A1 * | 7/2005 | Raymond et al. | 600/213 |
| 2005/0165283 A1 | 7/2005 | Hestad et al. | |
| 2005/0177028 A1 * | 8/2005 | Royce et al. | 600/210 |
| 2005/0192485 A1 | 9/2005 | Branch et al. | |
| 2005/0203625 A1 | 9/2005 | Boehm et al. | |
| 2005/0215866 A1 | 9/2005 | Kim | |
| 2005/0234304 A1 | 10/2005 | Dewey et al. | |
| 2005/0240209 A1 | 10/2005 | Hamada | |
| 2005/0245928 A1 | 11/2005 | Colleran et al. | |
| 2005/0277812 A1 * | 12/2005 | Myles | 600/231 |
| 2006/0004401 A1 | 1/2006 | Abernathie et al. | |
| 2006/0069315 A1 | 3/2006 | Miles et al. | |
| 2006/0106416 A1 | 5/2006 | Raymond et al. | |
| 2006/0235279 A1 | 10/2006 | Hawkes et al. | |

* cited by examiner

SURGICAL ACCESS SYSTEM AND METHOD OF USING THE SAME

CROSS REFERENCE TO RELATED APPLICATIONS

This application is a continuation-in-part of U.S. application Ser. No. 11/619,214 filed on Jan. 3, 2007, which is a continuation-in-part of U.S. application Ser. No. 11/458,662 filed on Jul. 19, 2006, the disclosures of which are expressly incorporated by reference herein in their entirety.

FIELD OF THE INVENTION

The present invention generally relates to access systems useful in various surgical procedures, and more particularly to an improved access system useful for minimally invasive surgical procedures.

BACKGROUND OF THE INVENTION

In the past, certain surgical procedures required relatively large incisions to be made into the body in order to gain visual and instrument access to a surgical site deep within the body. By way of example, surgical procedures on posterior spine elements may have required relatively large incisions to be made to effectively operate on the spine elements. These large incisions are generally undesirable as they may result in increased damage to muscle tissue, increased blood loss, prolonged pain to the patient as well as potential scarring.

More recently, however, many surgical procedures are conducted using minimally invasive techniques that seek to minimize some of the undesirable aspects of past procedures. Such techniques typically involve splitting the muscle tissue, as opposed to cutting the muscle tissue, which in turn causes less damage to the muscle, increases the recovery times, and reduces patient discomfort. Conventional retractors are used to hold the incision and passageway open through the soft tissue and muscle.

Once a path to the surgical site is established, an additional retractor or access port may be inserted through the incision to provide the necessary retraction so as to establish an unencumbered path to the surgical site. Thus, the retractor or access port effectively defines a working channel or space and provides visual and instrument access to the surgical site in a minimally invasive manner.

Although several minimally invasive access systems and techniques have been developed, there remains room for improvement. In particular, there is a need for an improved access system and method of using the same that addresses drawbacks of current access systems and associated procedures.

SUMMARY OF THE INVENTION

An improved access system that overcomes many of the drawbacks of previous devices includes a retractor for creating an access path between an incision site and a surgical site during a surgical procedure. The retractor includes a frame having a base member and a pair of generally parallel curved rails extending therefrom. The frame may further include a yoke or cross member opposite the base member with the rails extending therebetween. The retractor further includes a slide coupled to the frame and is capable of moving along the rails between a contracted position and an expanded position. A tubular member is coupled to the frame and includes a first and second blade portion that is inserted through the incision site to form at least a portion of the access path. In one embodiment, the first blade portion is coupled to the base member and extends therefrom. The second blade member is coupled to the slide and confronts the first blade member. The slide carrying the second blade member is configured to move along the rails to affect the size of the access path.

When the blade portions have been moved to the expanded position a gap is formed between the edges of the blade. In one embodiment of the invention, one or more side plates may be attached to the rails to fill the gap. The side plates are rotatable with respect to the rails between a first position and an angled position. A suitable tool may be used to rotate the side blades. In one embodiment, there are an infinite number of angular positions that the side plates may make with respect to the rails. In another embodiment, only a finite number of angular positions are defined. The side plates may also be secured to the rail. For example, in one embodiment, a set screw may be used to secure the side plate to the rail.

A method of using the retractor includes inserting a guide wire through an incision site to establish a path to a surgical site spaced therefrom. A guide rod is threaded over the guide wire, inserted through the incision site, and advanced toward the surgical site. An obturator is then inserted into the retractor when it is in the contracted condition. The obturator and retractor are then collectively threaded over the guide rod, inserted through the incision site, and advanced toward the surgical site. Once in place, the guide wire is removed. To remove the guide rod and obturator, the guide rod is pulled in a direction away from the surgical site. A distal end of the guide rod is configured to engage the distal end of the obturator so that movement of the guide rod pulls both the guide rod and obturator out of the retractor.

When the guide rod and obturator are removed, the blade portions may be moved relative to each other along the rails to retract the opening. A side plate may then be mounted to the retractor in order to fill the gap created between the blade portions. The side plates may be selectively rotated and fixed to the rails in a desired configuration.

These and other objects, advantages and features of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION OF THE PREFERRED EMBODIMENTS

Figure 1:
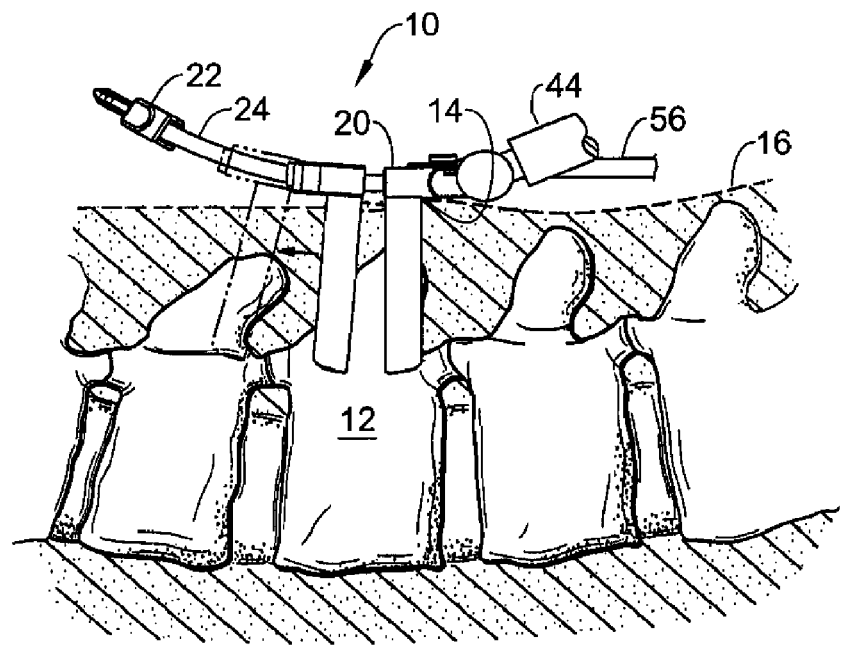
FIG. 1 is a cross-sectional view of a retractor in accordance with an embodiment of the invention used in posterior spine surgery.

Referring now to the figures, and to FIG. 1 in particular, a surgical access system according to the principles of the present invention includes a retractor 10 that may be used during a surgical procedure to expose and provide visual and instrument access to a surgical site 12 that is spaced from an incision site 14 on a patient 16. In one exemplary embodiment, the retractor 10 may be used for posterior spine surgery wherein certain spinal elements are located at the surgical site 12 and are spaced from an associated incision site 14 along the back of a patient 16. While the invention is shown and described in the context of posterior spinal surgery, the invention is not so limited as the retractor 10 may be used in a wide variety of surgical procedures wherein the surgical site is spaced from the incision site and unencumbered access to the surgical site via the incision site is desired. Thus the embodiment shown in FIG. 1 is only illustrative and those of ordinary skill in the art will recognize other surgical procedures that will benefit from the present invention.

Figure 3:
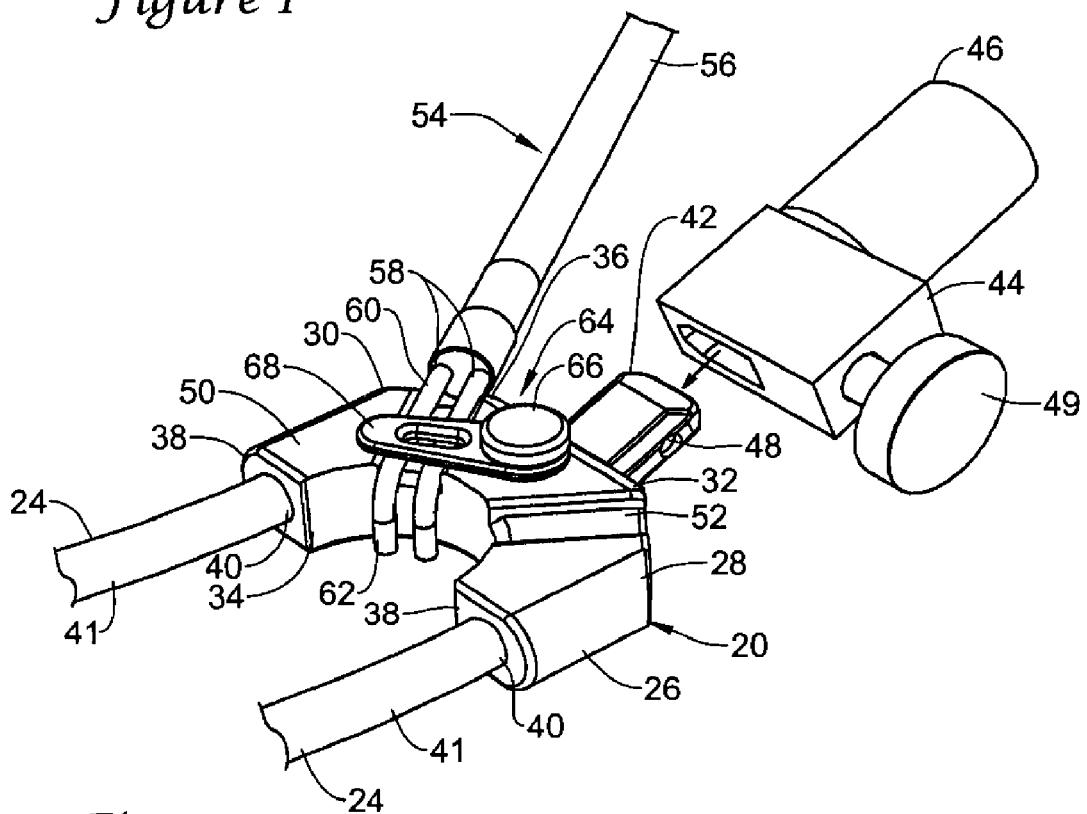
FIG. 3 is a partial perspective view of the base member and rails of the retractor shown in FIG. 2.
Figure 2:
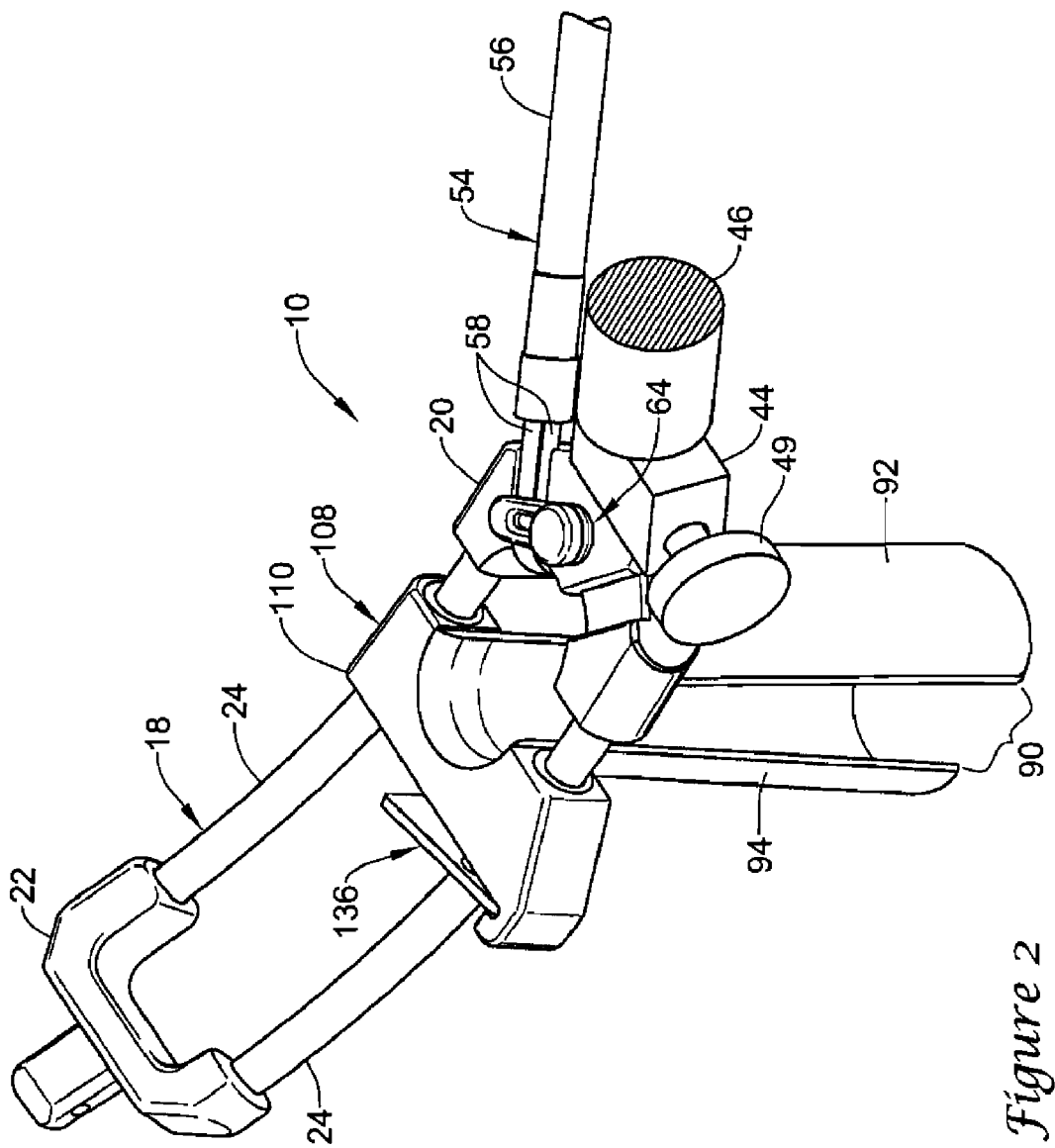
FIG. 2 is a perspective view of the retractor shown in FIG. 1.

As shown in FIGS. 1 and 2, the retractor 10 may include a frame 18 including a base member 20, and at least one, and preferably a pair of rails 24, extending from the base member 20. The frame may further include a yoke or cross member 22 opposite the base member 20 with the rails 24 extending therebetween. As shown in FIG. 1, the frame 18 may be positioned outside the body of the patient 16 and at a fixed location adjacent incision site 14 when used during a surgical procedure. As best shown in FIG. 3, the base member 20 may include a generally U-shaped body 26 having a pair of leg portions 28, coupled by a connecting portion 32 and defining an inner surface 34 and an outer surface 36. The inner surface 34 may be generally arcuate, and in an exemplary embodiment, is generally semi-circular in shape. An outer face 38 of each leg portion 28, 30 includes a blind bore 40 for receiving a first end 41 of respective rails 24. The rails 24 may be secured to the base member 20 by a suitable fastener (not shown). For example, the base member 20 may include at least one threaded fastener (e.g., screw) inserted into a corresponding threaded bore (not shown) formed in a bottom surface of base member 20 so as to intersect blind bore 40. The rails 24 may further include apertures (not shown) to receive the threaded fasteners to thereby secure the rails 24 to the base member 20. Those of ordinary skill in the art will recognize other fasteners suitable to secure the rails 24 to base member 20. Alternately, the base member 20 may be coupled with the rails 24 through a molding operation, such as an overmolding process. Other processes may also be used as recognized by one of ordinary skill in the art.

In one embodiment, the outer surface 36 of the base member 20 includes an outwardly projecting nipple 42 adapted to receive a connecting member 44 of a mounting arm 46 (which may be flexible), which is coupled to a support (e.g., operating table) and permits adjustment of the retractor 10 in relation to the patient 16. The nipple 42 may include at least one recess 48 adapted to receive a set screw 49 associated with the connecting member 44 to secure the mounting arm 46 to the nipple 42. The base member 20 may be formed of a sufficiently rigid polymer or other suitable materials as recognized by those of ordinary skill in the art. In one embodiment, the material from which base member 20 is formed may be radiolucent.

A top surface 50 of base member 20 may include one or more grooves 52 that extend between the inner and outer surfaces 34, 36. The grooves 52 are adapted to receive a portion of a light assembly 54 associated with the access system and operatively coupled to a power supply (not shown) via a suitable cord 56 so as to illuminate the surgical site 12 through the retractor 10. The light assembly 54 may be constructed using fiber optics and a suitable light source. In one embodiment, the light assembly 54 may include an end having at least one, and preferably two light tubes 58. Each of the light tubes 58 are J-shaped with a first, relatively straight portion 60 that extends along the groove 52 in top surface 50 and a hook portion 62 that extends downwardly toward the bottom surface of base member 20 and adjacent inner surface 34.

The base member 20 may further include a locking mechanism 64 that secures the light tubes 58 to the base member 20. In particular, the locking mechanism 64 includes a threaded thumb screw 66 received in a threaded bore (not shown) in the top surface 50 of base member 20 adjacent groove 52, and a lock bar 68 received on screw 66 and configured to extend across groove 52. The lock bar 68 is free to rotate around screw 66 when in a loosened condition. To secure the light tubes 58 in the groove 52, the lock bar 68 is positioned over the groove 52 and the thumb screw 66 tightened to prevent rotation of the lock bar 68 with respect to base member 20. The lock bar 68 then prevents upward movement of the light tubes 58 away from base member 20. In addition, the J-shape of the light tubes 58 further prevents any outward movement of the light tubes 58 away from the base member 20. Multiple grooves 52 may be provided to give some flexibility to the positioning of light assembly 54 with respect to the surgeon. Alternatively, the screw 66 may be in a fixed position and allow the lock bar 68 rotate to an interference fit with the light tubes 58 to hold the light tubes 58 in a desired position.

Figure 3A:
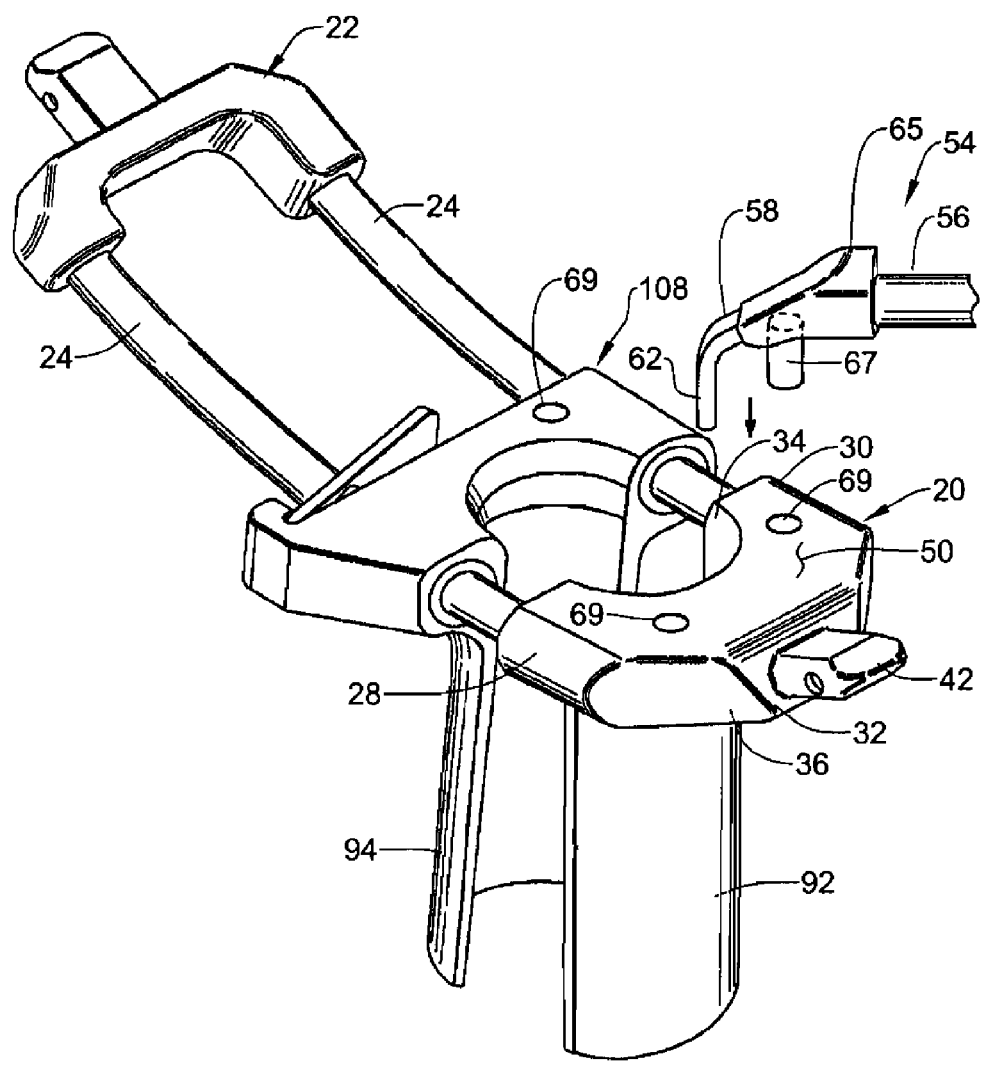
FIG. 3A is a perspective view of a light assembly in accordance with an embodiment of the invention.
Figure 3B:
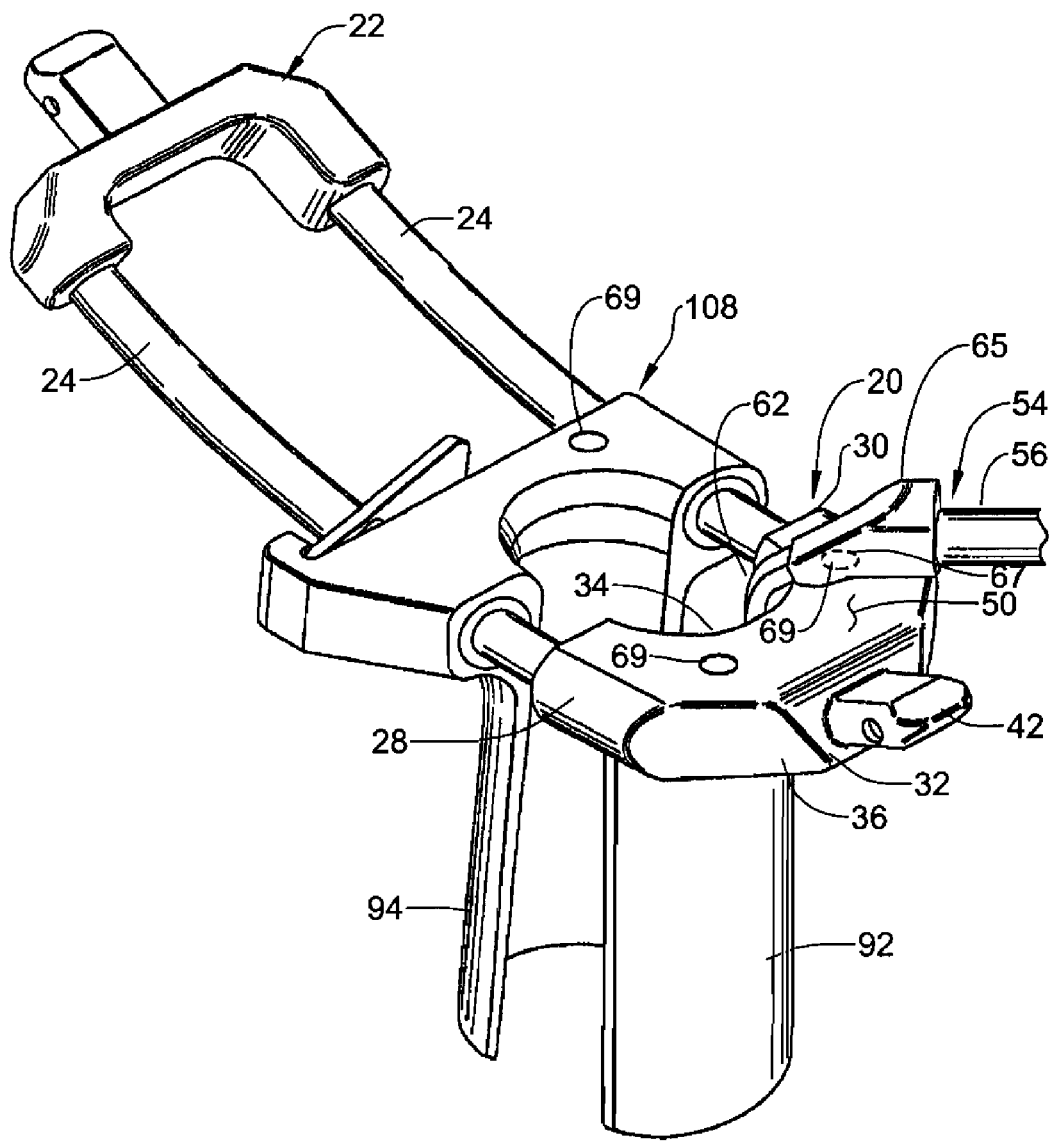
FIG. 3B is a perspective view showing the light assembly of FIG. 3A engaged with the retractor.

In an alternate embodiment, the light tubes 58 may be secured to the base member 20 in a different manner. In particular, and as shown in FIGS. 3A and 3B, the light assembly 58 includes an adaptor 65 from which the light tubes 58 extend. The adaptor 65 includes a post 67 that projects from a lower surface of the adaptor 65 in a direction generally parallel to the hook portion 62 of the light tubes 58, as shown in FIG. 3A. The post 67 is adapted to be releasably received in an aperture 69 in the top surface 50 of the base member 20. To this end, the post 67 may fit within aperture 69 in a friction fit. Alternately, a locking mechanism may be utilized to secure the adaptor 65 to the base member 20. For example, the one of the post 67 or aperture 69 may include a spring detent (e.g., a spring loaded ball detent) and the other of the post 67 or aperture 69 may include a recess for receiving the detent. When the post 67 is inserted into the aperture 69, the spring detent engages the recess to secure the adaptor 65 to the base member 20. Those of ordinary skill in the art will recognize other mechanisms to releasably secure the adaptor 65 with the base member 20. For example, a spring loaded pin attachment may be used.

As shown in FIG. 3B, when the adaptor 65 is coupled to the base member 20, the hook portion 62 of the light tubes 58 extend downwardly toward the bottom surface of the base member 20 and adjacent the inner surface 34 to illuminate the surgical site 12 through the retractor 10. The engagement of the post 67 with the aperture 69, through the friction fit or other locking mechanism as discussed above, prevents the undesired movement of the light tubes 58 relative to the base member 20. Similar to the previous embodiment, multiple apertures 69 may be provided in the base member 20 as well as at other locations of the retractor 10 to give some flexibility to the positioning of the light assembly 54 with respect to the surgeon.

Figure 4:
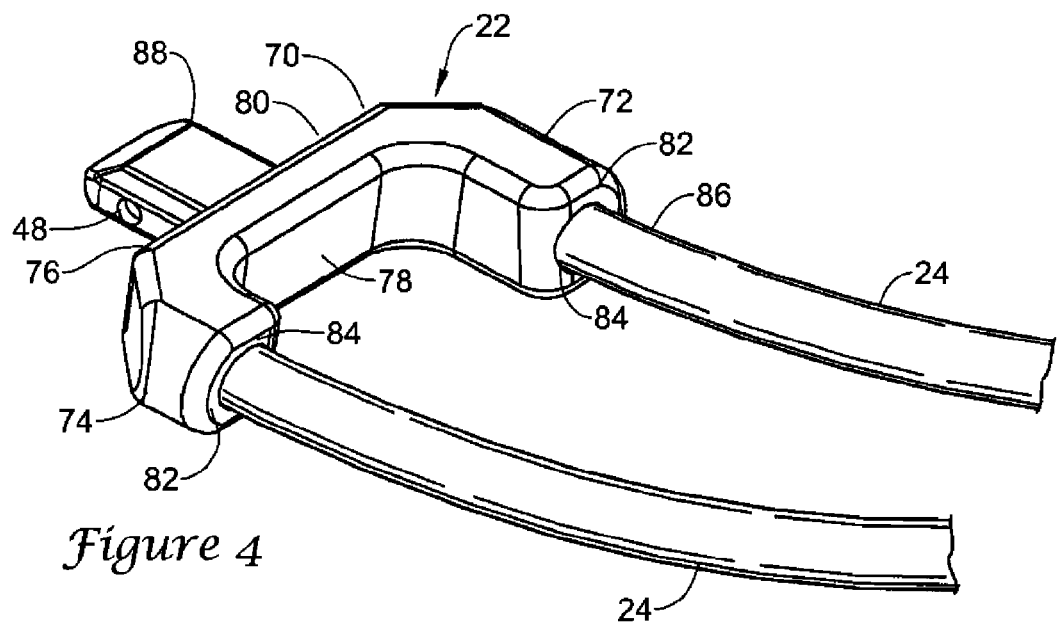
FIG. 4 is a partial perspective view of the yoke or cross member and rails of the retractor shown in FIG. 2.

As shown in FIG. 4, the cross member 22 has a similar construction to base member 20 and includes a generally U-shaped body 70 having a pair of leg portions 72, 74 coupled by a connecting portion 76 and defining an inner surface 78 and an outer surface 80. An outer face 82 of each leg portion 72, 74 includes a blind bore 84 for receiving a second end 86 of rails 24. The rails 24 may be secured to the cross member 22 by a suitable fastener. For example, the cross member 22 may include at least one threaded fastener (e.g., screw) inserted into a corresponding threaded bore (not shown) formed in a bottom surface of cross member 22 so as to intersect blind bore 84. The rails 24 may further include apertures to receive the threaded fasteners to thereby secure the rails 24 to the cross member 22. Those of ordinary skill in the art will recognize other fasteners suitable to secure the rails 24 to cross member 22. Alternately, the yoke member 22 may be coupled with the rails 24 through a molding operation, such as an overmolding process. Other processes may also be used as recognized by one of ordinary skill in the art, such as screw attachment, welding, or an adhesive bond.

The outer surface 80 of the cross member 22 may include an outwardly projecting nipple 88 adapted to receive a connecting member 44 of a mounting arm 46 (see FIG. 3) which is coupled to a support and permits adjustment of the retractor 10 in relation to the patient 16. Providing nipples on both sides of retractor 10 provides some flexibility in locating the mounting arm 46 in relation to the surgeon. One or both nipples 42, 88 may be used to locate the retractor 10 in relation to the body. The nipple 88 is constructed in the same manner as nipple 42 and may include at least one recess 48 adapted to receive a set screw 49 associated with the connecting member 44 to secure the mounting arm 46 to the nipple 88. The cross member 22 may be formed of a polymeric material, metal, or other suitable materials as recognized by those of ordinary skill in the art. In one embodiment, the material from which cross member 22 is formed may be radiolucent.

Figure 5A:
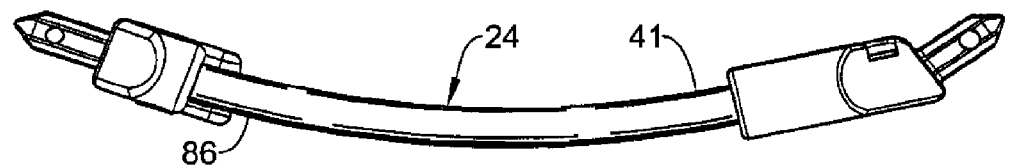
FIG. 5A is a side elevation view of a retractor in accordance with one embodiment of the invention and illustrating the curvature of the rails.
Figure 5B:
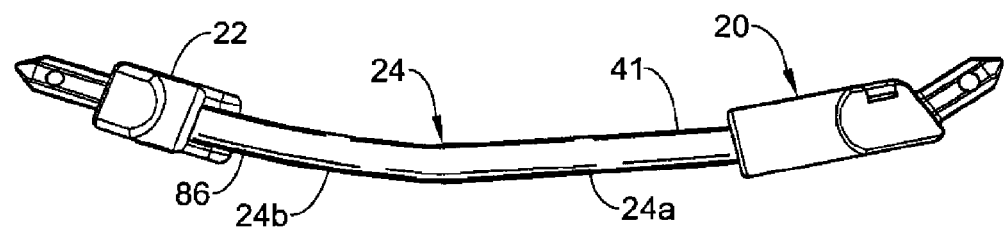
FIG. 5B is a side elevation view of a retractor in accordance with another embodiment of the invention and illustrating the curvature of the rails.

Referring to FIGS. 5A and 5B, in one aspect of the present invention, the rails 24 of frame 12 are not straight (i.e., lying along a single plane) along at least a portion of their length but rather may be generally curved from the first end 41 to the second end 86. In particular, as discussed in more detail below, certain benefits may be achieved if the curvature of the rails 24 matches or otherwise corresponds to structure, such as bone structure, at the surgical site 12. In one exemplary embodiment, the curvature of rails 24 may be configured to generally match the natural lordosis of the lumbar region of the spine. The invention is not so limited as the curvature of the rails 24 may be configured to generally match the curvature of other regions of the spine or other structures in the body that are the focus of surgical procedures that would benefit from the invention. The curvature of the rails 24 may be relatively constant (i.e., a portion of a circle with a specified radius of curvature) or may vary from the first end 41 to the second end 86, depending on the specific application. For instance, FIG. 5A illustrates rails 24 that curve in a continuous manner from the first end 41 to the second end 86. The invention, however, is not so limited. For example, the curvature of rails 24 may be achieved through discontinuous segments, either straight or curved, that as a whole approximate a curve. In an alternative embodiment, the rails 24 may be curved along at least a portion of their length and generally straight along another portion of their length. Thus, as shown in FIG. 5B, the rails 24 may include a first generally straight, linear section 24a and a second curved section 24b coupled thereto that collectively define a curved path along rails 24. Alternatively, the rails 24 may have sections with different radii or a continually changing radius. The rails 24 may be made from a wide range of suitable materials that provide sufficient rigidity to frame 12, such as for example stainless steel, titanium, aluminum, durable plastics, or other suitable materials known to those of ordinary skill in the art.

As shown in FIG. 2, the retractor 10 further includes a segmented tubular member 90 coupled to frame 18 and adapted to be inserted into the body of patient 16 through the incision site 14 so as to create an access path to the surgical site 12 within the body. The tubular member 90 includes blade portions 92, 94 capable of movement relative to each other along rails 24 to increase the effective opening of the access path. The increase in the effective opening is achieved by splitting and stretching the muscle as opposed to cutting, which provides certain advantages as previously discussed. The blades 92, 94 may include a taper at their distal ends that facilitate the insertion of the blades 92, 94 through the incision and to the surgical site 12. In an exemplary embodiment, the blades 92, 94 are formed from titanium, durable polymers, and other suitable materials known to those of ordinary skill in the art. In one embodiment, the blades 92, 94 may be formed from a radiolucent material.

Figure 6:
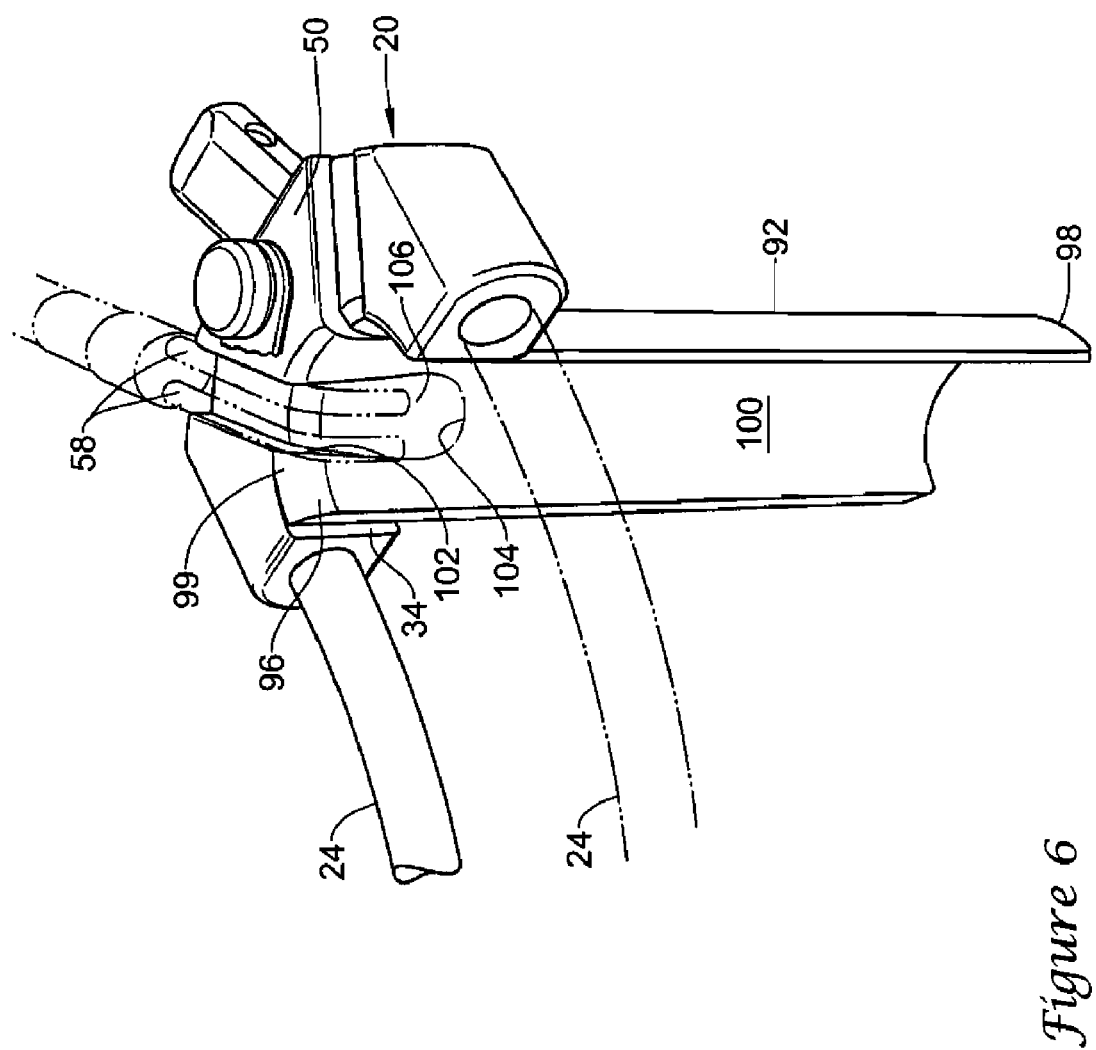
FIG. 6 is a perspective view similar to FIG. 3 but showing a blade portion coupled to the base portion.

As shown in FIGS. 2 and 6, tubular member 90 includes a first blade portion 92 having a proximal end 96 coupled to base member 20 and a distal end 98 extending away from the bottom surface of base member 20. The proximal end 96 of blade portion 92 is adapted to be coupled to base member 20 along inner surface 34. Thus, in one embodiment, the blade portion 92 may be generally semi-circular to match the semi-circular shape of the inner surface 34. The blade portion 92 may be rigidly secured to base member 20, such as through welding, fasteners such as screws, adhesives, etc. Those of ordinary skill in the art will recognize a wide range of fasteners or other ways to secure the blade portion 92 to the base member 20. The base member 20 and blade portion 92 may also be constructed as a unitary structure. The invention is not limited to rigid securement between the blade portion 92 and the base member 20. In another aspect of the invention, the blade portion 92 may be removably secured to base member 20. This would allow, for example, the blade portion 92 to be removed and replaced with another blade portion. The other blade portion may be configured differently for use in a specific application. For instance, depending on the specific application, the length of the blade portion 92 may have to be altered. In this case, the existing blade portion could be removed and another blade portion having a shorter or longer length could be coupled to base portion 20. Such a features facilitates the use of retractor 10 in a wide range of applications.

Figure 6A:
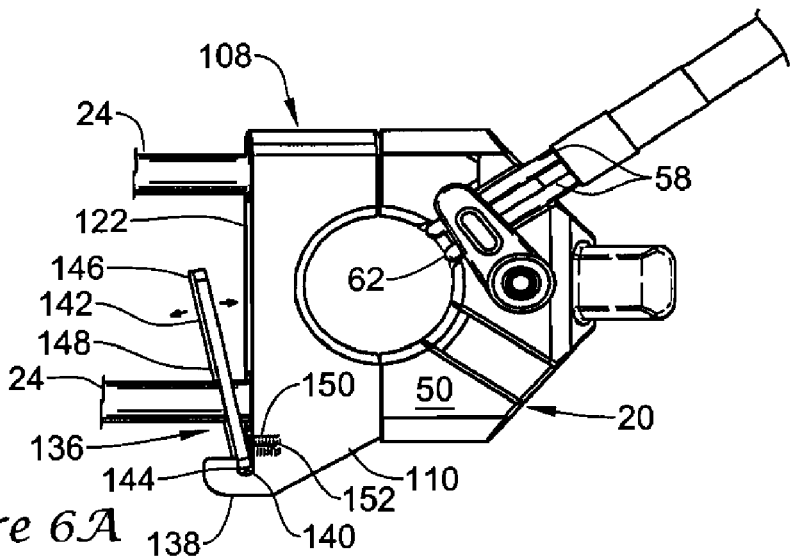
FIG. 6A is a top view of the retractor shown in FIG. 2.

The proximal end 96 of blade portion 92 may include an outward projecting lip 99 that mates with inner surface 34 so as to form a smooth transition between the top surface 50 of base member 20 and the inner surface 100 of blade portion 92. The proximal end 96 of blade portion 92 may also be configured to accommodate the light tubes 58 (shown in phantom) in an improved, unobtrusive manner. In particular as shown in FIGS. 6 and 6A, the proximal end 96 of blade portion 92 includes a notch 102 and a recess 104 formed by a tapered wall portion 106 in the wall of blade portion 92. The notch 102 is configured so that an upper edge of the tapered wall portion 106 forms a smooth transition with the bottom wall of groove 52. The recess 104 is configured to house the hook portion 62 of light tubes 58 that extend along blade portion 92. In this way, the light tubes 58 are able to provide illumination to the surgical site without projecting into the access path created by the inner surface 100 of blade portion 92. Thus, the light assembly 54 does not occlude the exposure of the surgical site 12 and the possibility of hitting or catching an instrument on the light assembly 54 is eliminated or significantly reduced. The tapered wall portion 106 not only forms the recess in which light tubes 58 are housed, but also sufficiently reflects the light generated by light tubes 58 so as to effectively illuminate the surgical site 12.

Figure 7:
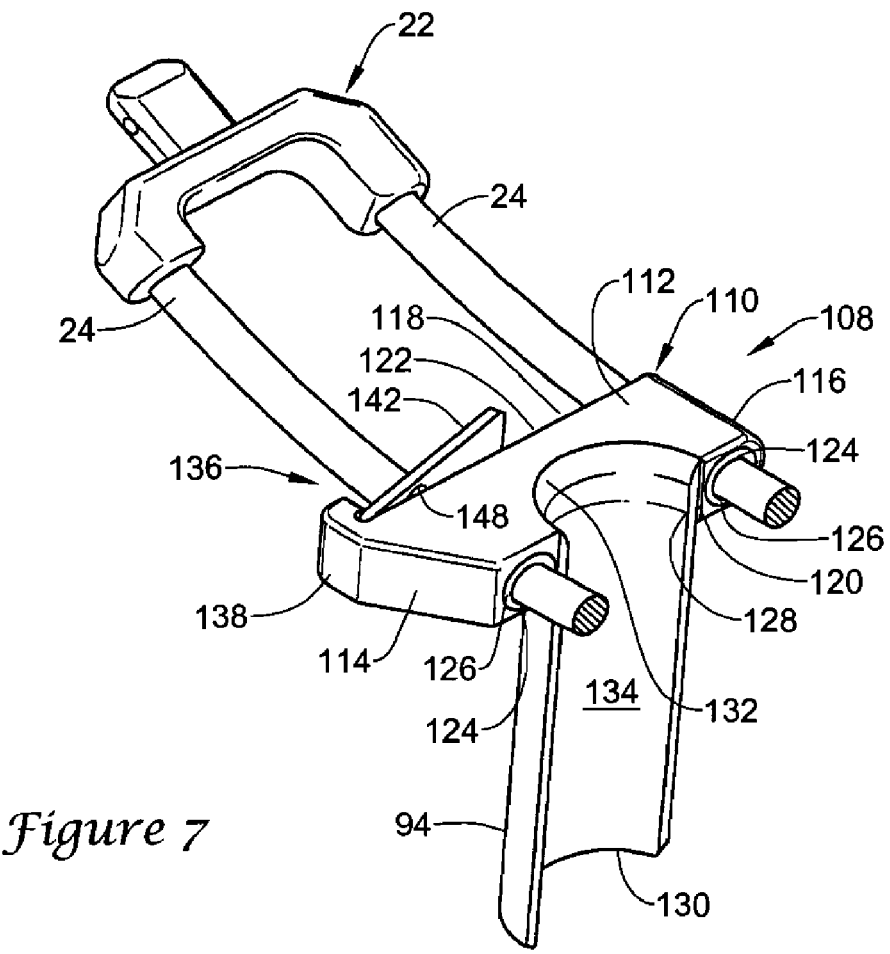
FIG. 7 is a partial perspective view of the slide of the retractor shown in FIG. 2.

Tubular member 90 also includes a second blade portion 94 movable relative to first blade portion 92 (FIG. 2). To this end, the retractor 10 further includes a slide 108 movably coupled to frame 18. As shown in FIG. 7, the slide 108 includes a hub member 110 having a generally U-shaped body 112 with a pair of leg portions 114, 116 coupled by a connecting portion 118 and defining an inner surface 120 and an outer surface 122. The inner surface 120 is generally arcuate, and in an exemplary embodiment, is generally semi-circular in shape. Each leg portion 114, 116 includes a through bore 124 for receiving rails 24 therethrough and permitting movement of the hub member 110 along rails 24 between a contracted position wherein the hub member 110 is located adjacent base member 20 and an expanded position wherein the hub member 110 is spaced from base member 20 (FIG. 2). Each of the through bores 124 may include a low-friction bushing 126 that facilitates movement of the hub member 110 along the curved rails 24. For example, in one embodiment, the outer surface of the bushing 126 is generally cylindrical and therefore is substantially straight in order to match a straight through bore 124 in hub member 110. The inner surface of the bushing 126, however, is curved in order to match the curvature of the rails 24. In this way, the slide 108 moves easily along the rails 24 to facilitate enhanced use of the retractor 10.

Still referring to FIG. 7, slide 108 further includes second blade portion 94 having a proximal end 128 coupled to hub member 110 and a distal end 130 extending away from the bottom surface of hub member 110. The proximal end 128 of blade portion 94 is adapted to be coupled to hub member 110 along inner surface 120. Thus, in one embodiment, the blade portion 94 may be generally semi-circular to match the semi-circular shape of the inner surface 120. The blade portion 94 may be rigidly secured to hub member 110 or may be removably attached thereto allowing the blade portion 94 to be changed out as explained above. The proximal end 128 of the blade portion 94 may include an outwardly projecting lip 132 that mates with inner surface 120 so as to form a smooth transition between the top surface of hub member 110 and the inner surface 134 of blade portion 94. Although not shown here, one of ordinary skill in the art will recognize that the slide 108 may also include grooves in hub member 110 and a notch and recess in blade portion 94 that permits the light assembly 54 to be coupled to the access system 10 via the hub member 110 in the manner described above.

Slide 108 includes a locking mechanism 136 to selectively permit relative movement between the hub member 110 and the rails 24. As shown in FIGS. 6B and 7, the hub member 110 includes a J-shaped tab 138 positioned outside and adjacent rail 24 and extending away from the outer surface 122 of hub member 110 to define a groove or channel 140 between the tab 138 and outer surface 122. The locking mechanism 136 includes a lock bar 142 having a first end 144 a second end 146, and an aperture 148 therein positioned adjacent first end 144 and adapted to receive rail 24 therethrough. The first end 144 of lock bar 142 is positioned in channel 140 when the rail 24 passes through aperture 148 and operates as a pivot point about which lock bar 142 may pivot. The lock bar 142 is pivotable between an open position wherein the rail 24 slides freely through the aperture 148 and a closed or locked position, where engagement between the aperture 148 and the rail 24 prevents relative movement of the hub member 110 relative to rail 24 and thus, locks the slide 108 to the frame 12.

When the lock bar 142 is in the open position, the hub member 110 may be freely moved along the rails 24, such as through a manual process, so as to separate the second blade portion 94 from the first blade portion 92. When the lock bar 142 is in the locked position, the rail 24 is canted with respect to the lock bar 142 so that a portion of the aperture 148 engages with a portion of the rail 24 to prevent any relative movement therebetween. In an exemplary embodiment, the lock bar 142 is biased toward the locked position. For example, the outer surface 122 of the hub member 110 may include a bore 150 adapted to receive a spring 152 that engages the lock bar 142 so as to bias the lock bar 142 toward the locked position. To move the hub member 110, a surgeon or other medical professional would apply a force to the second end 146 of lock bar 142 which would move the lock bar 142 to the opened position and allow the operator to move the slide 108 relative to the rails 24. When the desired position is reached, the force on lock bar 142 would be removed and the lock bar 142 would, under the bias of the spring 152, move back to the locked position to fix the position of the slide 108 relative to the rails 24. The locking mechanism 136 as described above may also operate as a one-way lock where moving the slide 108 away from the base member 20 automatically opens the lock bar 142 without the application of an operator's force on the second end 146 of lock bar 142. When the slide 108 stops moving away from the base member 20, the locking mechanism 136 automatically locks to the rail 24 and any movement of the slide 108 back toward the base member 20 is prevented.

Figure 8A:
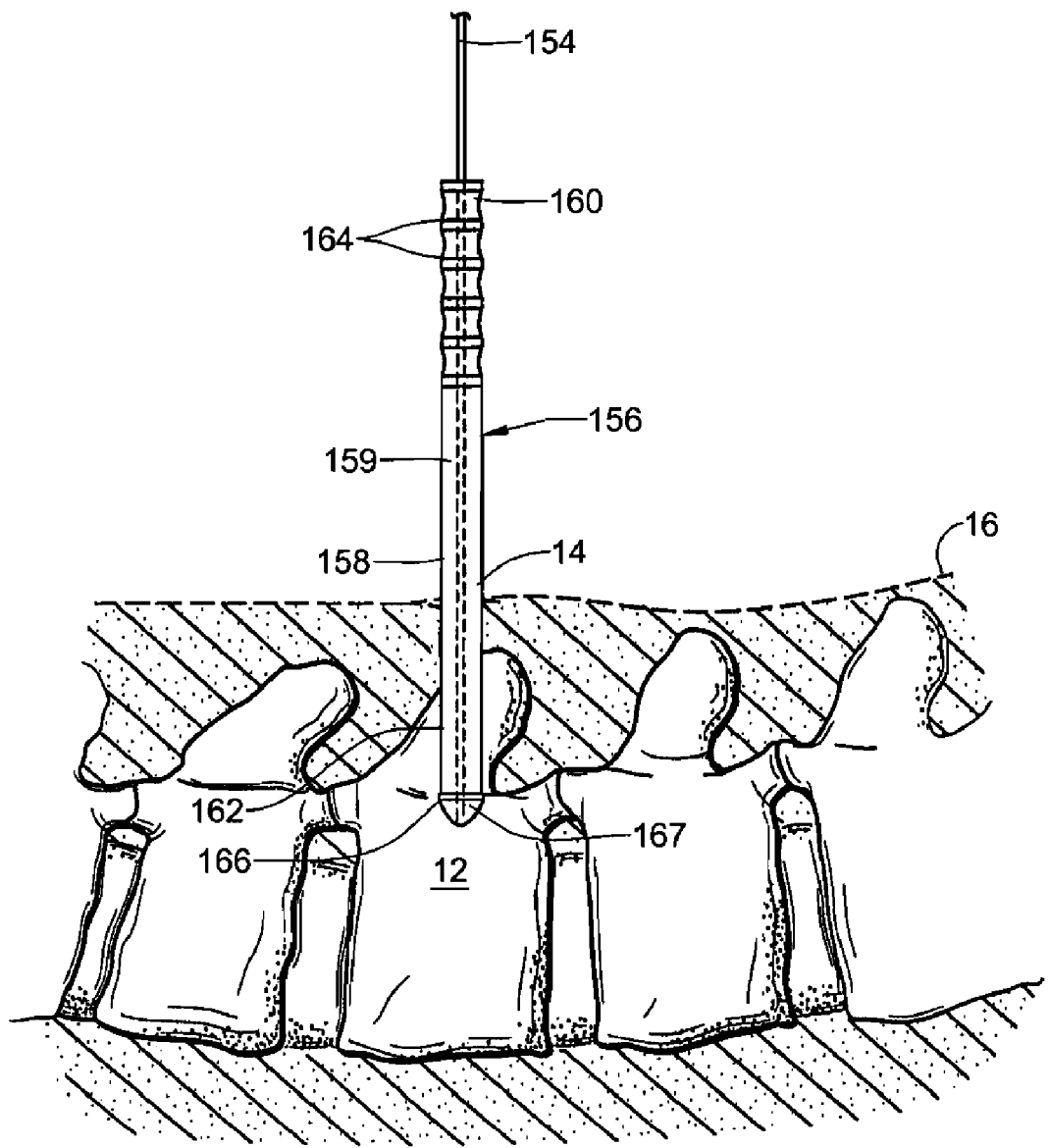
FIGS. 8A-8D are sequential illustration depicting the insertion of the retractor of FIG. 2 into the body of a patient.

Use of the access system as described above for an exemplary surgical procedure having a surgical site spaced from an incision site will now be described in reference to FIGS. 8A-8D. In an exemplary surgical procedure, an incision is made, for example in the skin, to form an incision site 14 proximate to an intended surgical site 12. As shown in FIG. 8A, guide wire 154, such as a k-wire, is inserted into the incision site 14, through the tissue, and to the surgical site 12 to establish a pathway from the incision site 14 to the surgical site 12. With the guide wire 154 inserted, a guide rod 156 is threaded onto the guide wire 154 and through the incision site 14. Alternatively, the guide rod 156 may be inserted through the incision site 14 without the use of the guide wire 154. The guide rod 156 is configured to create an opening through the tissue between the incision site 14 and the surgical site 12 by splitting and stretching the tissue as opposed to cutting the tissue. The guide rod 156 includes a generally cylindrical elongated body 158 having a central passage 159 through which the guide wire 154 extends, a proximal end 160 is adapted to be outside the body and a distal end 162 is adapted to be positioned near the surgical site 12. The proximal end 160 includes annular ridges 164 to facilitate gripping by a surgeon or other medical professional to work the guide rod 156 through the tissue and toward the surgical site 12. The distal end 162 includes an enlarged tip portion 166 whose purpose is explained in more detail below. The tip portion 166 includes a tapered region 167 to facilitate insertion of the guide rod 156 through the tissue.

Figure 8B:
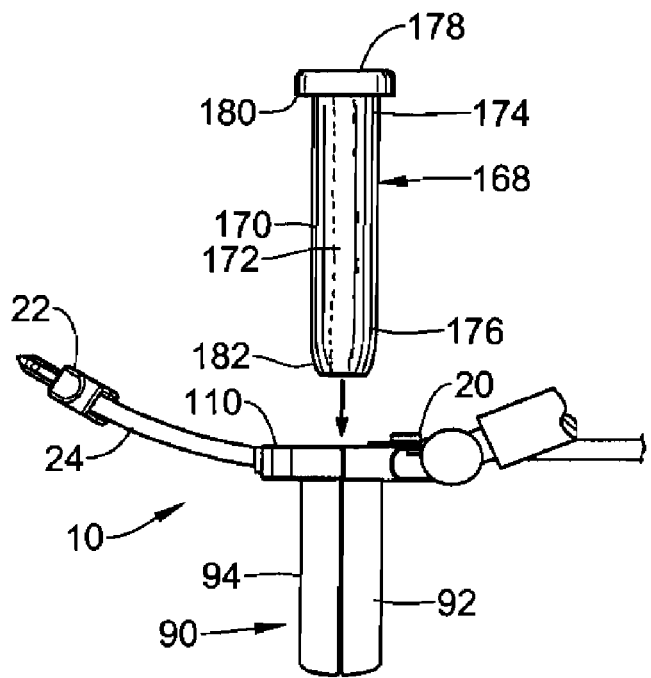

To insert the retractor 10 through the incision site 14 so as to create the access path to the surgical site 12, a second insertion step is performed using an obturator 168. As shown in FIG. 8B, the obturator 168 includes a generally cylindrical elongated body 170 having a central passage 172 through which the guide rod 156 extends, a proximal end 174 adapted to be outside the body, and a distal end 176 adapted to be positioned at or near the surgical site 12. The proximal end 174 includes an annular flange 178 extending radially outward from body 170 to define a shoulder 180. The distal end 176 of obturator 168 includes a tapered region 182 to facilitate insertion of the obturator 168 through the tissue and to the surgical site 12.

Figure 8C:
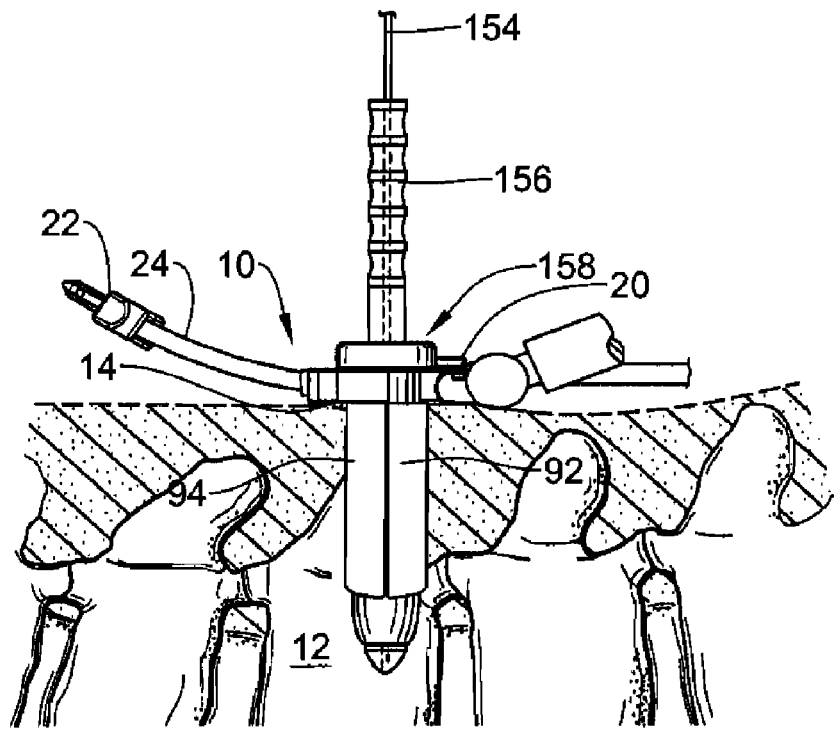

As shown in FIG. 8B, in an exemplary embodiment, before the obturator 168 is threaded over the guide rod 156, the obturator 168 is coupled to the frame 12 and tubular member 90 so as to position the retractor 10 within the body during the second insertion step. To this end, the hub member 110 is positioned in its contracted position so as to be adjacent base member 20. When in the contracted position, the first and second blade portions 92, 94 cooperate to generally form a closed cylindrical tube. The inner diameter of the of the tube formed by the inner surfaces 100, 134 of blade portions 92, 94 is slightly larger than the outer diameter of the elongated body 170 of obturator 168 and thus obturator 168 may be inserted therein. The flange 178 on obturator 168 is larger than the inner diameter of the cylindrical tube and thus contacts the top surfaces of the base member 20 and hub member 110 along shoulder 180. When the obturator 168 is properly seated in the tubular member 90 when in the contracted position, the distal end 176 extends beyond the distal ends 98, 130 of blade portions 92, 94, as shown in FIG. 8C. In one embodiment, the distal ends 98, 130 of blade portions 92, 94 are located at, or proximal of, tapered region 182 so as to provide a smooth transition between the increasingly larger components of retractor 10.

Figure 8D:
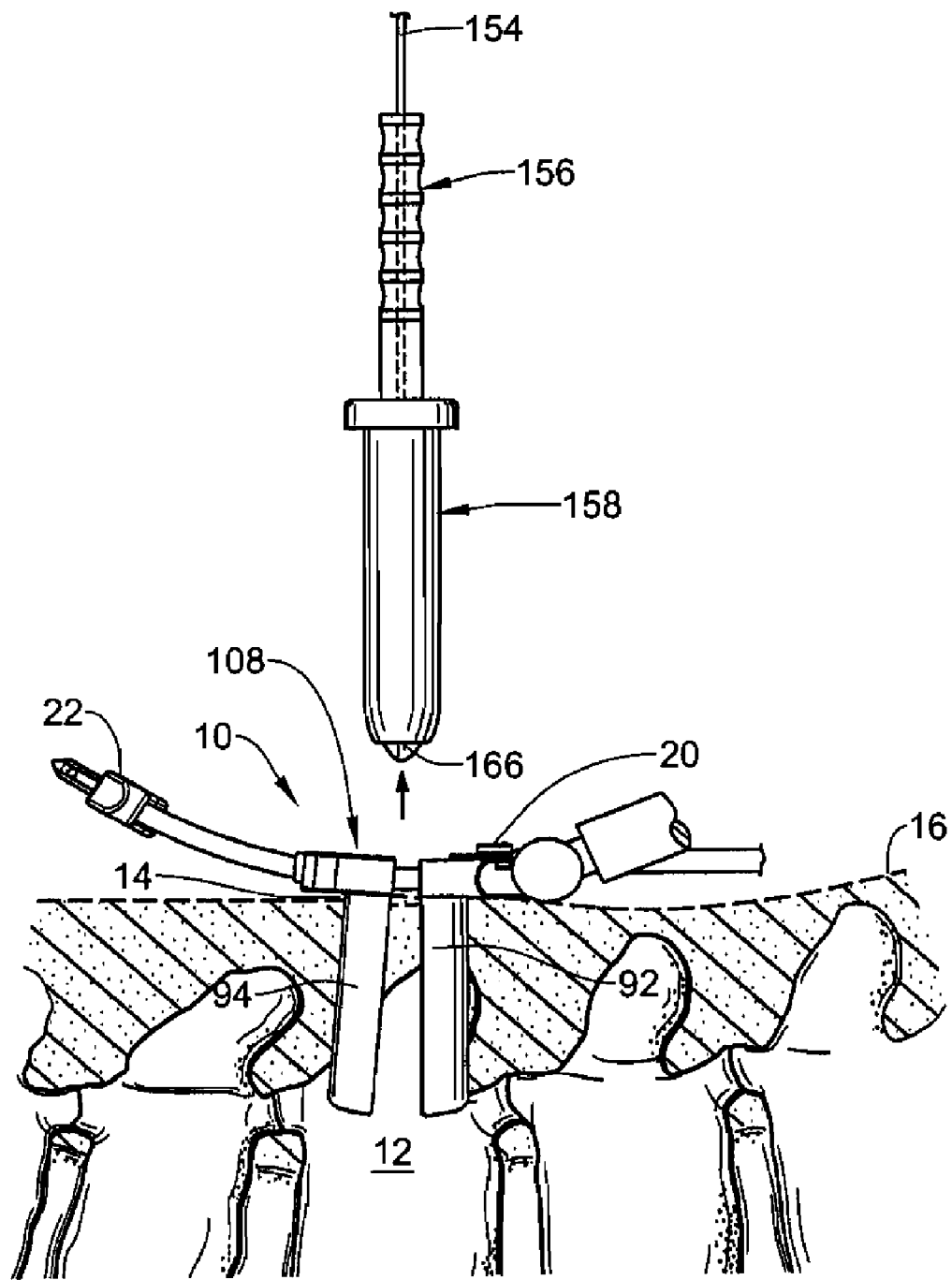

As shown in FIG. 8C, the obturator 168 and retractor 10 are inserted through the incision site 14 using the guide rod 156 as a guide so as to properly locate the retractor 10 within the body of the patient 16. The guide rod 156 and obturator 168 may then be removed from the body leaving only the retractor 10. To this end, when the retractor 10 is properly positioned in the body, the distal end 176 of obturator 168 is proximal of the enlarged tip portion 166 of guide rod 156. In this way, and as shown in FIG. 8D, when the guide rod 156 is pulled away from the surgical site 12, the enlarged tip portion 166 engages the distal end 176 of obturator 168 to also move obturator 168 away from the surgical site 12. Thus, by moving the guide rod 156 away, both guide rod 156 and obturator 168 are removed, leaving the retractor 10 positioned in the body of the patient 16.

With the access system 10 in the body, the slide 108 may be moved to increase the effective opening at the incision site 14. In particular, a pliers-type tool, as is known in the art, may be used to move the hub member 110 away from the base member 20 from its contracted position to an expanded position thereby moving the second blade portion 94 relative to the first blade portion 92 to increase the opening at the incision site 14. The retractor 10 in an expanded position is shown in FIG. 8D. Once in the expanded position, the locking mechanism 136 on the hub member 110 locks the hub member 110 and the second blade portion 94 along rail 24 as explained above.

The movement of the slide 108 along the curved rails 24 provides certain benefits not achieved in some prior art devices. By way of example, when the curvature of the rails approximates the curvature of the spine in, for example, the lumbar region, then the relative distance between the distal end of the second blade portion 94 and the bone structure of the spine is maintained even as the slide 108 is moved along the rails 24. Thus, there is no inadvertent or undesired contact between the second blade portion 94 and the spine during the movement. Moreover, maintaining the spacing between the distal end of the second blade portion 94 and the spine prevents any surrounding tissue from creeping into the access path or working space which would otherwise occlude exposure of the surgical site 12.

In addition, the curvature of the rails 24 provides an additional benefit. Due to the curvature of the rails 24, as the slide 108 moves along the curved rails 24, the access path created by first and second blade portions 92, 94 no longer has straight walls, e.g., a cross dimension spanning from the first blade 92 to the second blade 94 that remains constant from the incision site to the surgical site. Instead, because the second blade portion 94 remains substantially perpendicular to the rail 24, and rail 24 is curved, the second blade portion 92 becomes angled with respect to the first blade portion 92 so that the cross dimension spanning from the first blade 92 to the second blade 94 progressively increases in a direction from the incision site 14 to the surgical site 12. Such a configuration maintains a minimized cross dimension between the blades 92, 94 near the incision site 14 but increases the cross dimension in a direction toward the surgical site 12. Thus, the minimal invasiveness of the surgical procedure may be maintained while enhancing the exposure of the surgical site 12 away from the incision site 14.

The diverging configuration of the second blade portion 94 as described above, that results from the curvature of the rails 24 also provides a mechanism for preventing the surrounding tissue, which has been displaced by movement of second blade portion 94, from forcing the retractor 10 away from the surgical site 12. In essence, because the cross dimension between the first and second blade portion 92, 94 increases in a direction from the incision site 14 to the surgical site 12, the surrounding tissue imposes a net force on the second blade portion 94 in the direction of the surgical site 12. Thus, due to this configuration, the surrounding tissue imposes forces that, in essence, maintain the position of the retractor 10 in relation to the surgical site 12. This then eliminates or reduces any external forces necessary to maintain the position of the retractor 10 within the body.

Figure 9:
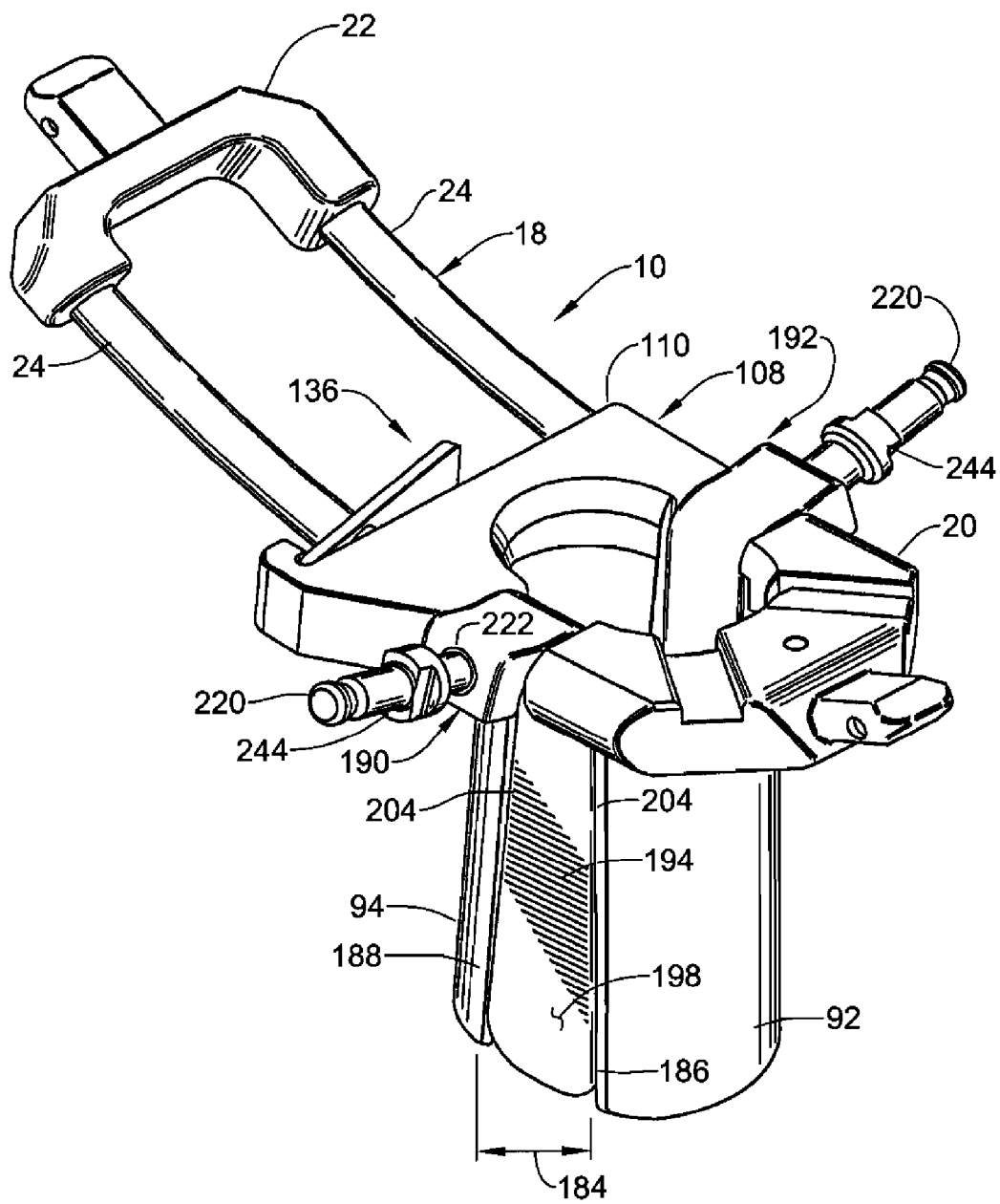
FIG. 9 is a perspective view of an embodiment of the retractor shown in FIG. 2 but having side plates.

As shown in FIG. 9, as the slide 108 is moved to its expanded position, the blade portions 92, 94 move apart from each other to form opposed gaps 184 between the side edges 186, 188 on first and second blade portions 92, 94 respectively (one shown). Consequently, the surrounding tissue proximate gaps 184 tends to encroach or creep around the side edges 186, 188 and may occlude the exposure of the surgical site 12. In an exemplary embodiment, the retractor 10 may further include side plates 190, 192 adapted to be mounted to rails 24 to prevent or reduce the encroachment of surrounding tissue into the access path through gaps 184. As the construction and operation of side plates 190, 192 are substantially the same, only side plate 190 will be described in detail herein.

Figure 10:
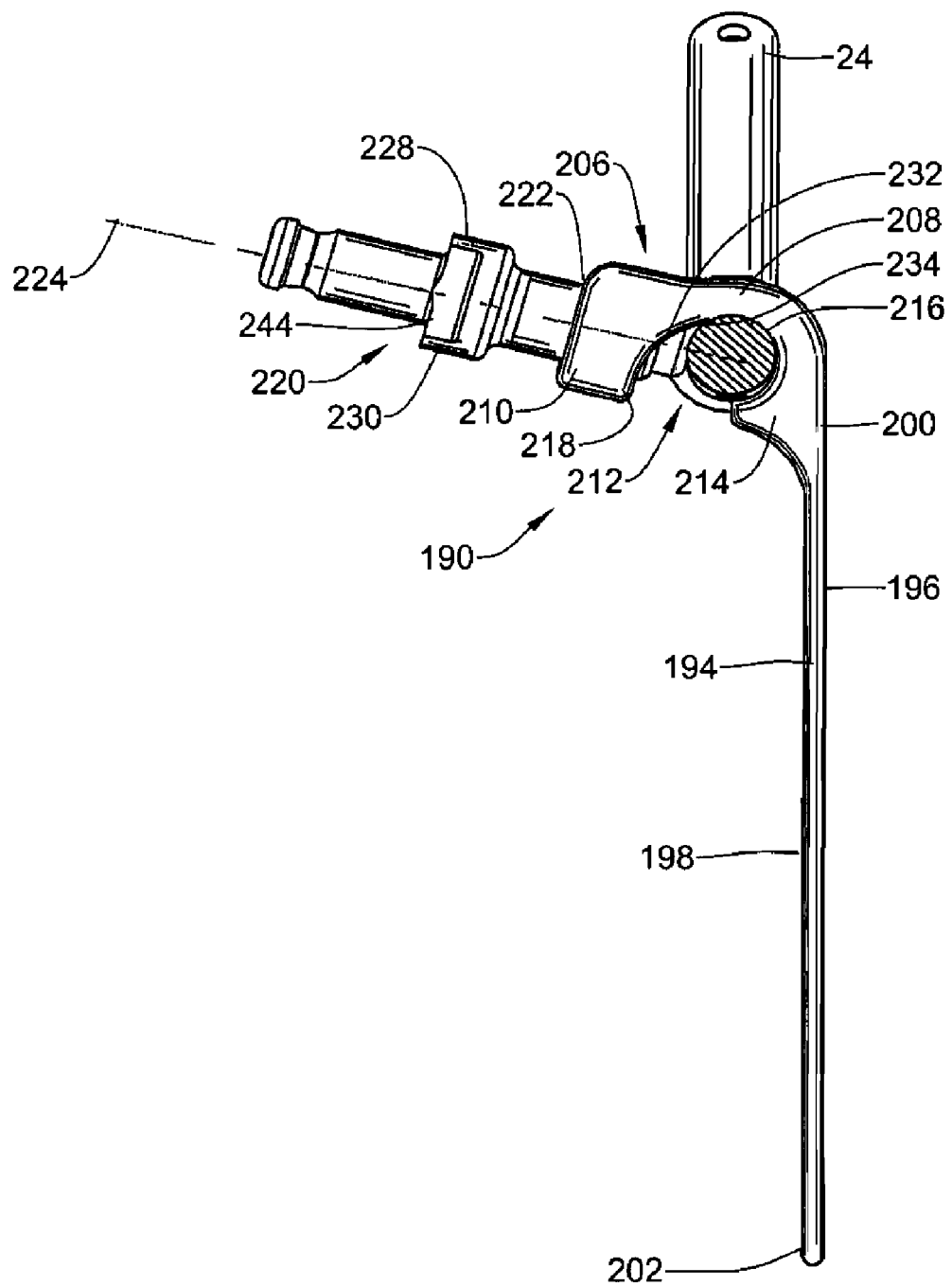
FIG. 10 is a partial cross-sectional view of the retractor shown in FIG. 9.

Referring to FIGS. 9 and 10, side plate 190 includes a generally flat, elongated body 194 having an inner surface 196 adapted to form part of the access path, an outer surface 198 adapted to face the surrounding tissue, a proximal end 200 adapted to be adjacent rail 24, a distal end 202 adapted to be positioned through the incision site 14 and towards the surgical site 12, and a pair of side edges 204 extending between the proximal and distal ends 200, 202. A cross-dimension of the side plate 190 may be configured to correspond to the shape of the gap 184 between the two blade portions 92, 94 when in the expanded position (FIG. 9). Thus, for example, the cross-dimension of the side plate 190 may increase in a direction from the proximal end 200 to the distal end 202. In addition, the length of the side plate 190 may correspond to the length of the side edges 186, 188 of blades 92, 94. However, as those of ordinary skill in the art will recognize, the invention is not so limited as a shorter or longer side plate 190 may be used depending on the specific application.

The proximal end 200 of side plate 190 includes a mounting member 206 for mounting the side plate 190 on rail 24. In one embodiment, the mounting member 206 has a J-shaped configuration with a top leg 208 coupled to and extending generally perpendicular to body 194 and a down-turned flange 210 coupled to top leg 208 and extending toward distal end 202. The J-shaped mounting member 206 defines an engagement region 212 bounded by the body 194, top leg 208, and down-turned flange 210, and adapted to receive the rail 24 therein. The outer surface 198 of slide plate 190 includes a projecting rib 214 that partially bounds a bearing surface 216 having a shape that corresponds to the shape of a portion of the rail 24. Thus, for example, in an exemplary embodiment, the bearing surface 216 may be semi-circular in shape so as to closely receive a portion of the circumference of rail 24. The rib 214 also cooperates with down-turned flange 210 to define an opening 218 to engagement region 212 that is larger than the cross dimension (e.g., diameter) of the rail 24 so as to permit the rail 24 to pass into the region 212 and bear against bearing surface 216. To mount the side plate 190 on rail 24, the proximal end 200 of side plate 190 is positioned between blade portions 92, 94 when in an expanded position and adjacent rail 24 so that rail 24 passes through the opening 218 and is seated against bearing surface 216.

Side plate 190 further includes an attachment member that secures the side plate 190 to the rail 24. In one embodiment, the attachment member includes a set screw 220 for securing the side plate 190 to rail 24. As shown in FIGS. 9 and 10, the down-turned flange 210 includes an aperture 222 therethrough and aligned along an axis 224 that intersects the bearing surface 216 in the engagement region 212. The aperture 222 includes internal threads (not shown). The set screw 220 includes a proximal end 228 defining a head 230 and a distal end 232 defining a contacting surface 234. Set screw 220 further includes external threads (not shown). The internal threads of aperture 222 cooperate with external threads on screw 220 such that rotation of the screw 220 in a first direction causes the screw 220 to advance along axis 224, moving contacting surface 234 toward bearing surface 216. Rotation of the screw 220 in an opposite direction causes the screw to withdraw along axis 224, moving contacting surface 234 away from bearing surface 216. In this way, the set screw 220 may be in a release position allowing the rail 24 to pass through opening 218 and to be seated in bearing surface 216. The set screw 220 may then be moved to an engaged position by rotating the set screw in the first direction so that the contacting surface 234 contacts the rail 24 and sufficiently compresses the rail 24 between the contacting and bearing surfaces 234, 216 to prevent relative movement between the side plate 190 and rail 24.

Figure 10A:
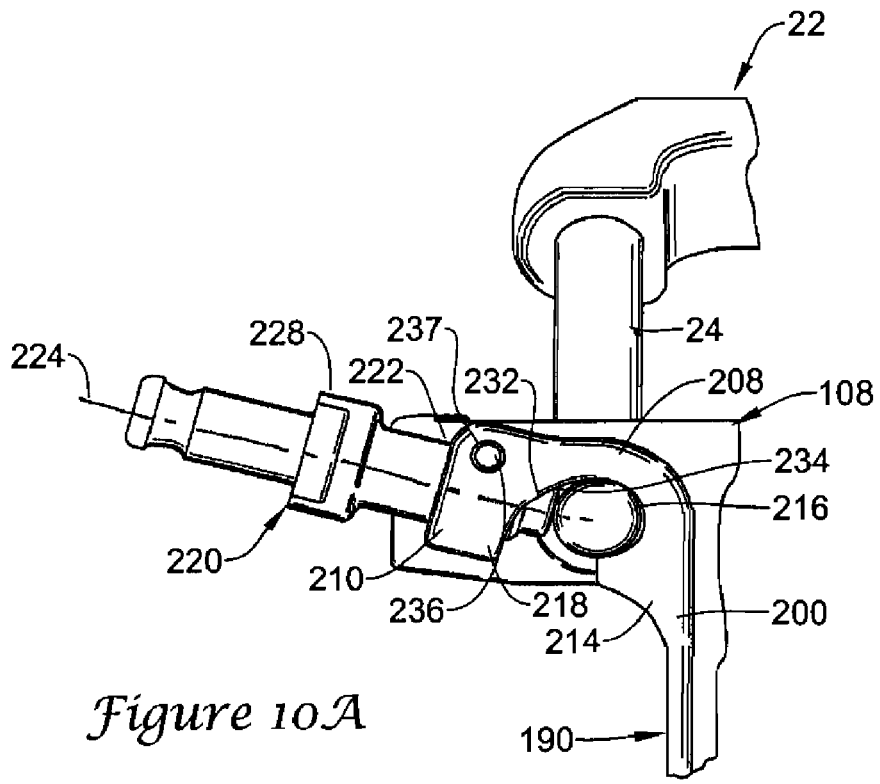
FIG. 10A is a partial cross-sectional view of a retractor in accordance with an alternate embodiment of the invention.
Figure 10B:
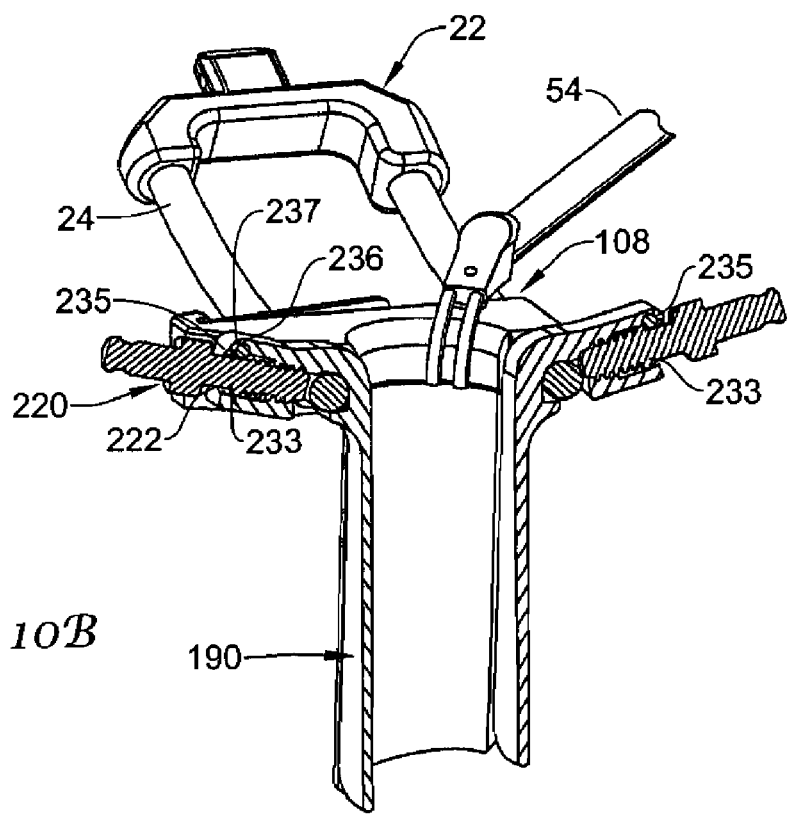
FIG. 10B is a partial cross-sectional view of the retractor shown in FIG. 10A.

As shown in FIGS. 10A and 10B, the attachment member may include a securing feature or mechanism that keeps the set screw 220 from becoming separated from the side plate 190. For instance, the securing mechanism prevents the set screw 220 from being withdrawn along axis 224 to the extent that the set screw 220 disengages from the side plate 190. To this end, the set screw 220 may include an annular rib 233 that increases the cross dimension of the set screw 220 thereat so as to define a shoulder 235 between the rib and an adjacent, smaller cross dimension portion of the set screw 220. The rib 233 is adjacent to, but proximal of the threads that facilitate engagement of the set screw 220 in the aperture 222 in flange 210. When the set screw 220 is positioned in the aperture 222, the rib 233 is sized to fit therein, as shown in FIG. 10B.

In addition to the rib 233, the securing mechanism may further include a stop that cooperates with rib 233 so as to prevent movement of the rib 233 beyond the stop. In one embodiment, the stop includes an aperture or throughbore 236 formed in the flange 210 that intersects aperture 222. As shown in FIG. 10A, the aperture may extend along an axis that is generally perpendicular to aperture 222. The aperture 236 is configured to receive a pin member 237 therein. The pin member 237 may be secured in the aperture by friction, welding, adhesive, and other techniques known to those of ordinary skill in the art. As shown in FIG. 10B, at least a portion of the pin member 237 projects into the aperture 222 through which the set screw 220 extends. The pin member 237 effectively reduces the cross dimension of the aperture 222 at the pin member 237. In particular, the cross dimension of the aperture 222 at the pin member 237 is less than the cross dimension of the set screw 220 at the rib 233. Accordingly, as the set screw 220 is being withdrawn along axis 224, the shoulder 235 of the rib 233 engages the pin member 237 to prevent any further movement of the set screw 220 away from the aperture 222. Thus, the set screw 220 is prevented from being completely disengaged from the side plate 190. Moreover, when the shoulder 235 engages the pin member 237, the set screw 220 is in the release position allowing the rail 24 to pass through opening 218 and to be seated in bearing surface 216.

Figure 11:
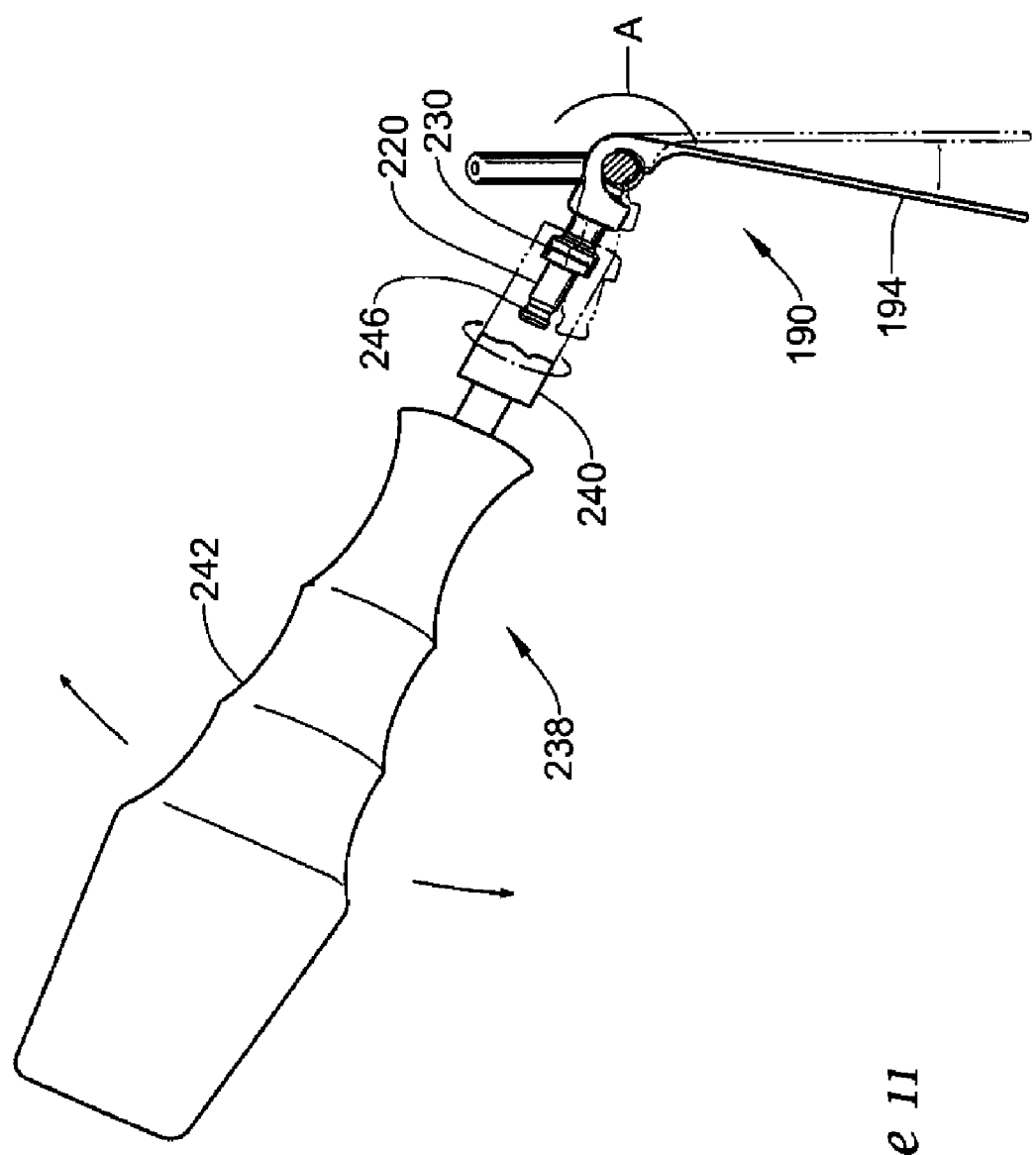
FIG. 11 is a partial cross-sectional view of the retractor similar to FIG. 9 and showing a tool for manipulating the side plate.

In one embodiment and as shown in FIG. 11, a suitable tool 238 may be used to rotate the set screw 220 between the release and engaged positions. To this end, the tool 238 may include a connector portion 240 and a handle portion 242. The connector portion 240 cooperates with head 230 such that rotation of the tool 238 rotates the set screw 220. For example, the connector portion 240 may include one or more ribs (not shown) that engage one or more flats 244 on the head 230. The handle portion 242 is configured to be easily grasped by a surgeon or other medical professional for rotating the tool 238 in order to advance or withdraw the set screw 220.

In another aspect of the invention, due to the particular configuration of the attachment member 220 described above, the side plate 190 is permitted to rotate about the rails 24 illustrated by arrow A when the set screw 220 is not in the engaged position. In particular, in an exemplary embodiment, the side plate 190 is free to continuously rotate about the rail 24 to effectively define an infinite number of angular positions of side plate 190 relative to rail 24. When mounted on rail 24, the side plate 190 defines a first position where the edges 186, 188 of blade portions 92, 94 and the side edges 204 of the side plate 190 lie in the same plane. This is shown in FIG. 9 and in phantom in FIG. 11. When both side plates 190, 192 are in the first position, the side plates 190, 192 cooperate with blade portions 92, 94 to define a substantially enclosed circumference along at least a portion of the access path between the proximal and distal ends of the blade portions (FIG. 9).

In one aspect of the invention, however, the side blades 190, 192 may be rotated on rails 24 to an angled position and then secured to the rails 24 using set screw 220 to maintain the angled position, as illustrated in FIG. 11. The side plates 190, 192 may be rotated outwardly and away from each other such that a cross dimension between the two plates 190, 192 at the incision site 14 is minimized, while the cross dimension between the two plates 190, 192 increases in a direction from the incision site 14 to the surgical site 12 to increase the exposure of the surgical site 12. Those of ordinary skill in the art will recognize that side plates may be used on just one or both rails 24.

In addition to rotating set screw 220 to secure the side plates 190, 192 to the rails, tool 238 may also be used to rotate the side plates 190, 192 to their desired angular positions. Thus, it is desired that the tool 238 be coupled to the set screw 220 in a secure, yet removable manner. To this end, set screw 220 may include an attachment member 246 and the tool 238 may also include an attachment member (not shown) that cooperate to provide a secure coupling between the tool 238 and set screw 220. For example, the attachment member 246 may be a quick-release type of connection that allows the tool 238 to be removed once the desired angular position is reached. Those of ordinary skill in the art will recognize a wide range of attachments that may secure the tool 238 to the set screw 220 in order to allow an operator to rotate or otherwise manipulate the side plates 190, 192 about the rail 24. In the embodiment shown and described herein, the tool 238 may be used to both rotate the side plates 190, 192 about rails 24, by providing a secure coupling to set screw 220, and to secure the side plates 190, 192 to the rails 24 by advancing/withdrawing the set screw 220 as explained above.

Figure 12B:
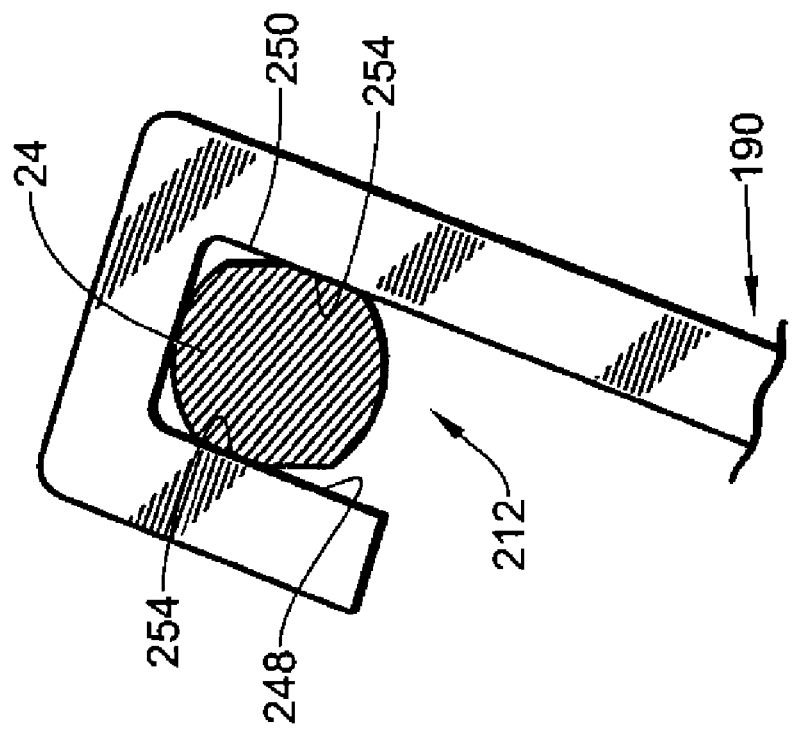
FIG. 12B is a cross-sectional view similar to FIG. 12A but showing the side plate in an angled position.
Figure 12A:
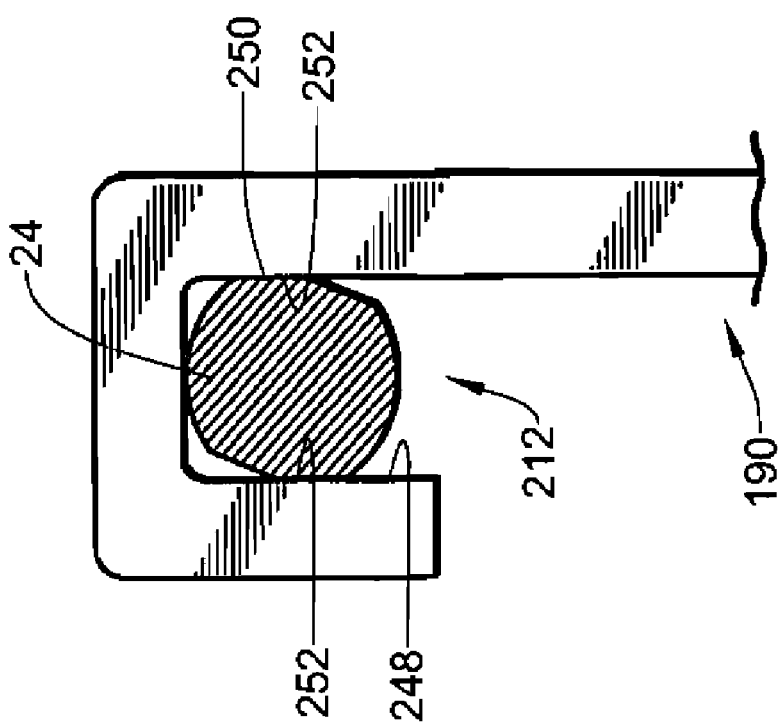
FIG. 12A is a cross-sectional view showing the coupling of a side plate and a rail in accordance to another embodiment of the invention with the plate in a first position.

The side plates 190, 192 may be secured in various angular positions in other ways. For example, in another embodiment, and as shown in FIGS. 12A and 12B in which like reference numerals refer to like features in FIG. 10, the engagement region 212 my include a pair of generally parallel, opposed walls 248, 250 that cooperate with opposed flats on rails 24. For instance, when the side plates 190, 192 are in the first position (i.e., aligned with blade portions 92, 94), shown in FIG. 12A, the walls 248, 250 engage flats 252 on rail 24 and rotation of the side plates 190, 192 is prevented. Flats may also be provided on rails 24 to position the plates 190, 192 in an angled position. For instance, as shown in FIG. 12B, flats 254 may be provided such that engagement of the walls 248, 250 with flats 254 places the side plates in an angled position. As those of ordinary skill in the art will appreciate, only a discrete number of angular positions of the side plates may be provided in this manner.

In use, the side plates may, in essence, substantially close the gaps 184 between the blade portions and prevent or reduce the likelihood of tissue creeping into the access path and occluding the exposure of the surgical site. Depending on the size of the gap 184, a single side plate may be used or multiple side plates may be positioned on each of the rails 24. In addition, a plethora of the side plates may be provided with each side plate having a different cross dimension to accommodate different size gaps. As mentioned above, a plethora of side plates may also be provided with each side plate having a different length. The invention is not limited to the number, size, geometry, etc. of the side plates as those of ordinary skill in the art recognize that the plates may be configured to suit a particular surgical application.

Figure 13:
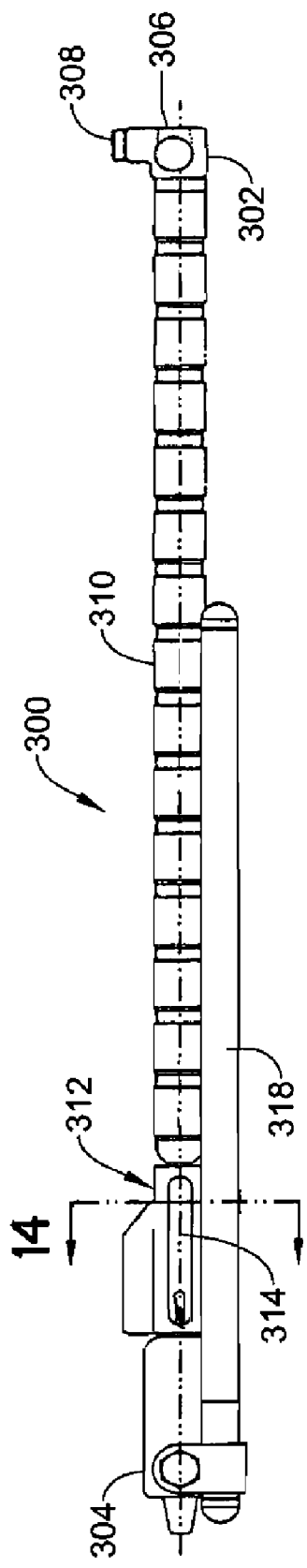
FIG. 13 is a side view of a mounting arm for use with a retractor in accordance with the invention.
Figure 14:
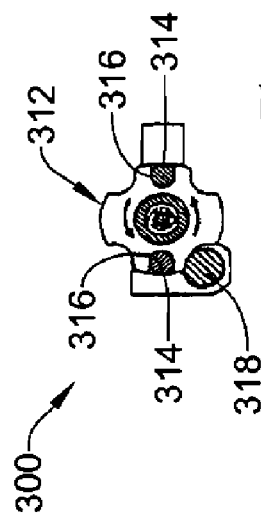
FIG. 14 is a cross-sectional view of the mounting arm in FIG. 13 along the line 14-14.

FIGS. 13 and 14 show an embodiment of a flexible mounting arm 300 that may be used with retractor 10 in accordance with the invention. The mounting arm 300 is a generally elongate member having a first end 302 and a second end 304. The first end 302 is adapted to be coupled to the retractor 10. In particular, the first end 302 is adapted to be coupled to the outwardly projecting nipple 42 on the base member 20 or the cross member 22. To this end, the first end 302 may include an aperture 306 for receiving nipple 42 therein. The first end 302 may further include a set screw 308 received in a separate aperture (not shown) that intersects aperture 306. The set screw 308 is adapted to secure the mounting arm 300 to the retractor 10 via nipple 42. The set screw 308 may include a securing mechanism to prevent the set screw 308 from becoming disengaged from the first end 302 of the mounting arm 300. For example and without limitation, the securing mechanism discussed above in relation to the side plate 190 may be used to prevent disengagement of the set screw 308 from the mounting arm 300.

The mounting arm 300 includes a flexible portion 310 that allows the arm to flex in essentially an infinite number of positions, thereby allowing the retractor 10 to be desirably placed in relation to the incision site 14 on patient 16. The flexible portion 310 includes a locking handle 312 that is movable between a first open position, in which the flexible portion 310 may be flexed to a desired position, and a second locked position, which fixes the shape of the flexible portion and prevents further flexing of the flexible portion 310. For example, in an exemplary embodiment, the locking handle 312 may be rotated to move between the first and second positions.

The locking handle 312 may include at least one, and preferably a pair of opposed handle rods 314 coupled to locking handle 312. The handle rods 314 are pivotally coupled to the locking handle 312 at one end thereof so as to move between a collapsed position and an extended position. In the collapsed position, the handle rods 314 are adjacent the locking handle 312, as shown in FIG. 14. As shown in this figure, the handle rods 314 may be disposed in recesses 316 of locking handle 312 when in the collapsed position. In the expanded position, however, the handle rods 314 project outwardly from the locking handle 312. In this way, a user can grip the extended handle rods 314 and apply an increased torque to the locking handle 312 to facilitate securing the locking handle in the second position, thereby fixing the shape of the flexible portion 310. As shown in FIG. 13, the mounting arm 300 further includes a connecting member 318 that is pivotally connected to the second end 304 of the mounting arm 300. The connecting member 318 is adapted to couple the mounting arm to a fixed support, such as an operating table.

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in numerous combinations depending on the needs and preferences of the user.

What is claimed is:

1. A surgical retractor for creating an access path between an incision site and a surgical site during a surgical procedure, comprising:
   a frame having a base member, a cross member, and a pair of generally parallel curved rails extending between said base member and said cross member;
a tubular member coupled to said frame and having a first blade portion and a second blade portion, said first and second blade portions capable of relative movement with respect to each other from a first contracted position to an expanded position by movement of at least one of said blade portions along said rails;
   at least one side plate connectable to at least one of said rails and in a gap between said first and second blade portions when in the expanded position, said side plate including an attachment mechanism for securing said side plate to said rail, the retractor having a securing mechanism for preventing the attachment mechanism from becoming disengaged from said side plate.

2. The surgical retractor of claim 1, wherein said side plate includes an aperture and said attachment mechanism includes a set screw, said set screw adapted to be received in said aperture and movable relative thereto between a secured position in which the side plate is secured to the rail and a release position in which the side plate is capable of being coupled to or removed from the rail.

3. The surgical retractor of claim 2, wherein the securing mechanism comprises:
   an annular rib on the set screw that defines a shoulder, the annular rib sized to fit within the aperture in the side plate; and
   a stop extending into the aperture, the stop adapted to engage the shoulder of the rib to prevent the set screw from disengaging from the aperture.

4. The surgical retractor of claim 3, wherein the stop comprises:
   a throughbore in the side plate that intersects the aperture; and a pin member disposed in the throughbore so that at least a portion of the pin projects into the aperture.

* * * * *